US006777191B1

(12) United States Patent
Springer et al.

(10) Patent No.: US 6,777,191 B1
(45) Date of Patent: Aug. 17, 2004

(54) USE OF FUNCTIONAL DERIVATIVES OF THE INTERCELLULAR ADHESION MOLECULE ICAM-1 IN DIAGNOSIS OF VIRAL INFECTION

(75) Inventors: Timothy A. Springer, Newton, MA (US); Donald E. Staunton, Chestnut Hill, MA (US)

(73) Assignee: Center for Blood Research, Inc., Boston, MA (US)

( * ) Notice: Subject to any disclaimer, the term of this patent is extended or adjusted under 35 U.S.C. 154(b) by 0 days.

(21) Appl. No.: 08/474,387

(22) Filed: Jun. 7, 1995

Related U.S. Application Data

(60) Division of application No. 08/420,720, filed on Apr. 11, 1995, which is a continuation of application No. 08/136,408, filed on Oct. 15, 1993, now abandoned, which is a continuation of application No. 07/514,033, filed on Apr. 27, 1990, now abandoned, which is a continuation-in-part of application No. 07/454,292, filed on Dec. 22, 1989, now abandoned, which is a continuation-in-part of application No. 07/324,073, filed on Mar. 16, 1989, now abandoned.

(51) Int. Cl.$^7$ ............................................... G01N 33/53

(52) U.S. Cl. ........................................ 435/7.1; 435/7.2

(58) Field of Search ................................. 435/7.1, 69.3, 435/7.2; 530/350, 395, 868; 514/2, 8

(56) References Cited

U.S. PATENT DOCUMENTS

| | | | |
|---|---|---|---|
| 5,235,049 A | * | 8/1993 | McClelland et al. |
| 5,304,636 A | * | 4/1994 | Blaas et al. |
| 5,589,453 A | | 12/1996 | Greve |
| 5,686,582 A | * | 11/1997 | Greve et al. ................. 530/402 |
| 5,831,036 A | * | 11/1998 | Springer et al. |
| 5,859,212 A | * | 1/1999 | McClelland et al. |
| 6,051,231 A | * | 4/2000 | Greve et al. |
| 6,143,298 A | * | 11/2000 | Greve et al. |
| 6,326,004 B1 | * | 12/2001 | Greve et al. |
| 6,436,403 B1 | * | 8/2002 | Springer et al. |
| 6,511,664 B1 | | 1/2003 | Springer et al. |
| 6,514,936 B1 | | 2/2003 | Greve et al. |

FOREIGN PATENT DOCUMENTS

EP          0 319 815          6/1989

OTHER PUBLICATIONS

Ngo et al. in The Protein Folding Problem and Tertiary Structure Prediction, 1994, Merz et al. (ED) Birkhauser, Boston MA, pp. 433 492–495.*
Kogan et al. J. Biol. Chem 270:14047–14055 (1995).*
Skolnick et al. Trends in Biotech 18:34–39 (2000).*
Staunton et al. Cell 52:925–933 (1988).*
Staunton, D. E. et al., Cell 61:243–254 (Apr. 20, 1990), "The arrangement of the immunoglobulin–like domains of ICAM–1 and the binding sites for LFA–1 and rhinovirus".*

Ruoslahti, E. et al., Synthetic Peptides in Biology and Medicine, pp. 191–197, "Synthetic peptides in the analysis of cell adhesion", 1985.*
Marlin et al. "A Soluble form of Intercellular Adhesion Molecule–1 Inhibits Rhinovirus Infection" Nature vol. 344 pp. 70–72, 1990.*
Marlin et al. Purified Intercellular Adhesion Molecule–1 (ICAM–1) is a Ligand for Lymphocyte Function—Associated Antigen1(LFA–1) Cell vol. 51, pp. 813–819, 1987.*
Abraham, G., et al., "Many Rhinovirus Serotypes Share the Same Cellular Receptor," *J. Virol.* 51(2):340–345 (1984).
Arruda, E., et al., "In Vitro Studies of the Antirhinovirus Activity of Soluble Intercellular Adhesion Molecule–1," *Antimicrob. Agents and Chemother.* 36(6):1186–1191 (1992).
Colonno, R. J., et al., "Isolation of Monoclonal Antibody that Blocks Attachment of the Major Group of Human Rhinoviruses," *J. Virol.* 57 (1):7–12 (1986).
Colonno, R. J., et al., "Human Rhinovirus Attachment Requires a Specific Cellular Receptor Protein," *J. Cell. Biochem. Suppl 10(part D)* :266 (1986).
Couch, R. B., "Rhinoviruses," in: *Virology*, Fields, B. N., et al., eds., New York: Raven Press, pp. 607–629 (1990).
Crump, C. E., et al., "In vitro Inhibitory Activity of Soluble ICAM–1 for the Numbered Serotypes of Human Rhinovirus,"*Antivir. Chem. and Chemother.* 4(6): 323–327 (1993).
Dustin, M. L., et al., "Induction by IL–1 and Interferon–γ: Tissue Distribution, Biochemistry, and Function of a Natural Adherence Molecule (ICAM–1)," *J. Immun.* 137(1):245–254 (1986).
Greve, J. M., et al., "The Major Human Rhinovirus Receptor is ICAM–1," *Cell* 56:839–847 (Mar. 10, 1989).
Hayden, F. G., et al., "Modification of Experimental Rhinovirus Colds by Receptor Blockade,"*Antivir. Res.* 9:233–247 (1988).
Keizer, G. D., et al., "Biochemical and Functional Characteristics of the Human Leukocyte Membrane Antigen Family LFA–1, Mo–1 and p150,95," *Eur. J. Immunol.* 15:1142–1147 (1985).
Martin, S., et al., "Functional Studies of Truncated Soluble Intercellular Adhesion Molecule 1 Expressed in *Escherichia coli*," *Antimicrob. Agents and Chemother.* 37(6):1278–1285 (1993).
Olson, N. H., et al., "Structure of a Human Rhinovirus Complexed with its Receptor Molecule," *Proc. Natl. Acad. Sci. USA* 90:507–511 (1993).

(List continued on next page.)

*Primary Examiner*—Phillip Gambel
(74) *Attorney, Agent, or Firm*—Sterne Kessler Goldstein & Fox P.L.L.C.

(57) ABSTRACT

The invention concerns the use of functional derivatives of ICAM–1 to treat viral infection. The invention also provides a vaccine to prevent such infection, and a diagnostic assay to determine the existence and extent of such infection.

3 Claims, 13 Drawing Sheets

OTHER PUBLICATIONS

Pober, J. S., et al., "Overlapping Patterns of Activation of Human Endothelial Cells by Interleukin 1, Tumor Necrosis Factor, and Immune Interferon," *J. Immunol.* 137:1893–1896 (1986).

Rothlein, R., et al., "A Human Intercellular Adhesion Molecule (ICAM–1) Distinct from LFA–1," *J. Immunol.* 137:1270–1274 (1986).

Rudinger, in: *Peptide Hormones*, Parsons, J. A. ed., Baltimore: University Park Press, pp. 1–7 (1976).

Sanchez–Madrid, F., et al., "Mapping of Antigenic and Functional Epitopes on the α–and β–Subunits of Two Related Mouse Glycoproteins Involved in Cell Interactions, LFA–1 and Mac–1," *J. Exp. Med. 158*:586–602 (1983).

Sanchez–Madrid, F., et al., "A Human Leukocyte Differentiation Antigen Family with Distinct α–Subunits and a Common β–Subunit," *J. Exp. Med. 158*:1785–1803 (1983).

Schipper, N. G., et al., "The Nasal Mucociliary Clearance: Relevance to Nasal Drug Delivery," *Pharmac. Res. 8(7)* : 807–814 (1991).

Sperber, S. J., et al., "Chemotherapy of Rhinovirus Colds," *Antimicrob. Agents and Chemother. 32(4)*:409–419 (1988).

Springer, T. A., et al., "LFA–1 and Lyt–2,3 Molecules Associated with T Lymphocyte Killing; and Mac–1, an LFA–1 Homologue Associated with Complement Receptor Function," *Immunol. Rev. 68*:171–195 (1982).

Springer, T. A., "The LFA–1, Mac–1 Glycoprotein Family and its Deficiency in an Inherited Disease," *Fed. Proc. 44*:2660–2663 (1985).

Staunton, D. E., et al., "A Cell Adhesion Molecule, ICAM–1, is the Major Surface Receptor for Rhinovirus," *Cell* 56:849–853 (Mar. 10, 1989).

Tomassini, J. E., et al., "Isolation of a Receptor Protein Involved in the Attachment of Human Rhinoviruses," *J Virol. 58(2)*:290–295 (1986).

Tomassini, J. E., et al., "cDNA Cloning Reveals that the Major Group Rhinovirus Receptor on HeLa Cells is Intercellular Adhesion Molecule 1,"*Proc. Natl. Acad. Sci. USA 86:*4907–4911 (1989).

* cited by examiner

FIG.1A

```
GGG CTG TTC CCA GTC TCG GAG GCC CAG GTC CAC CTG GCA CTG GGG GAC CAG AGG TTG AAC CCC ACA GTC ACC TAT GGC AAC GAC TCC TTC    867
 G   L   F   P   V   S   E   A   Q   V   H   L   A   L   G   D   Q   R   L   N   P   T   V   T   Y   G   N   D   S   F     243

TCG GCC AAG GCC TCA GTT GTG AGT GTC ACC GCA GAG GAC GAG GGC ACC CAG CGG CTG ACC TGT GCA GTA ATA CTG GGG AAC CAG AGC CAG GAG    957
 S   A   K   A   S   V   S   V   T   A   E   D   E   G   T   Q   R   L   T   C   A   V   I   L   G   N   Q   S   Q   E     273

ACA CTG CAG CAG ACA GTG ACC ATC TAC AGC TTT CCG GCG CCC AAC GTG ATT CTG ACG AAG CCA GAG GTC TCA GAA CCG GAG GTG ACA GTG     1047
 T   L   Q   Q   T   V   T   I   Y   S   F   P   A   P   N   V   I   L   T   K   P   E   V   S   E   G   T   E   V   V     303

AAG TGT GAG GCC CAC CCT AGA GCC AAG GTC ACG CTG AAT GGG GTT CCA GCC CAG CCA CCG CTG GGC CCG CGG GCC CAG CTG CTC CTG AAG GCC   1137
 K   C   E   A   H   P   R   A   K   V   T   L   N   G   V   P   A   Q   P   P   L   G   P   R   A   Q   L   L   L   K   A  333

ACC CCA GAG GAC AAC GGC CGC AGC TTC TCC TGT TCT GCA ACC CTG GAG GTG GCC GGC CAG CTT ATA CAC AAG AAC CAG ACC CGG GAG CTT     1227
 T   P   E   D   N   G   R   S   F   S   C   S   A   T   L   E   V   A   G   Q   L   I   H   K   N   Q   T   R   E   L     363

CCT GTC CTG TAT GGC CCC CCG CGA CTG GAC CGA CCT GAC TGT CCG GGA AAC TGG ACG TGG CCA GAA AAT TCC CAG CAG ACT GTC ACT CCA ATG TGC CAG 1317
 P   V   L   Y   G   P   P   R   L   D   E   R   D   C   P   G   N   W   T   W   P   E   N   S   Q   Q   T   V   T   P   M   C   Q  393

GCT TGG GGC AAC CCA CTG CCC GAG CTC AAG TGT CTA AAG GAT GGC ACC TTC CCA CTG CCC ATC GGG GAA TCA GTG ACT GTC ACT GAG GAT     1407
 A   W   G   N   P   L   P   E   L   K   C   L   K   D   G   T   F   P   L   P   I   G   E   S   V   T   V   T   R   D     423

CTT GAG GGC ACC TAC CTC TGT CGG GCC AGG AGC ACT CAA GGG GAG GTC ACC CGG GAG GTG ACC GTG AAT GTG CTC TCC CCG CGG TAT GAG     1497
 L   E   G   T   Y   L   C   R   A   R   S   T   Q   G   E   V   T   R   E   V   T   V   N   V   L   S   P   R   Y   E     453
```

FIG. 1B

```
ATT GTC ATC ATC ACT GTG CTA GCA GTC GCC GCA GTC ATA ATG GGC ACT GCA GGC CTC TAT AAC CGC CAG AAG ATC AAG 1587
 I   V   I   I   T   V   V   A   A   A   V   I   M   G   T   A   G   L   S   T   Y   L   Y   N   R   Q   K   I   K  483

AAA TAC AGA CTA CAA CAG GCC CAA AAA GGG ACC CCC ATG AAA CCC AAC ACA CAA GCC ACG CCT CCC TGA ACCTATCCCGGACAGGCCCTCTTCCT 1683
 K   Y   R   L   Q   Q   A   Q   K   G   T   P   M   K   P   N   T   Q   A   T   P   P   *                              505

CGGCCCTTCCATATGGTGGCAGTCGTCCCACACTGAAGAGAGTGAAGACATATGCCATGCAGCTACCTACCCGGCCCTGGAGCCGGAGGACAGGGCATTGTCCTCAGTCAGATA 1802
CAACAGCATTTGGGCCCATGGTACCTGCCACACTGCAGTCTGATCTGTAGTCACATGGCATCTGATCTGTAGTCACATACAACTGGAAATACTGAGCCCACAGACTTA 1921
TAAAGTCTAGCCTGATGAGAGGGAGAAGTGGTGGGGAGACATAGCCCTCCACCATGCCCCACCACTTCCTGAGGATGCCAGTCCAGCTGTCTGCCTGCTACTGTCTGCCACTGATGACAGACTIA 2040
CAGAAGAAGTGGCCTCCATAGACATGTGTAGCATGTACAACAAAGCCCACCAACACTTGGCCACTGTGCTGTCACCCTTGATGATATGTATTT 2159
ATTCATTGTTATTTACCAGTCTATTATTGAGTGTCTTTTATGTACCGTATTGGAAGATCAAATGGGCTGGCAAAAGATACTTCTCATTGCCCACATCTCCGCACAAAGCAC 2278
TGTACAGGTTGTACACTGCAGAGAGTGCCTGAGAGTTCACAGGTCAGAGATTACCCAGTGAGTGCCCAGGGAATATGCCCAAAAACTGACACCTTTGTTAGCCACCTGATTTTTCTATGGCGACTCCACTACATTTCTGCCAG 2397
TATATGGACTGGTAATGCGTAACACTGCAGTGGTCATGCTGGACATGAGTGCCCAGGGGAATATGCCCAAGGTATTGGAGGACTCCCTCCAGCTTTGGGCTCAGTGATCCTCCCACCTGCAGTGGTGTCAGTAGCTCAGATGCAGCTC 2516
TGTTCACAATGACACTCAGCGGTCATGCTGGACATGAGTGCCCAGGGGGCCAAGGTATTGGAGGACTCCCTCCAGCTTTGGGCTCAGTGATCCTCCCACCTGCAGT 2635
CAGTTTCCTGCATGATCAGGTCCTGCAAGCTGCAGTGCCACACGCCCTGACCTTTGACCTTTGGGCTCAGTGATCCTCCCACCTGCAGTGGT 2754
AGCTCTCGCTCTGCACCACCACCTGGCAATTTGATTTTTTTTTTTCAGAGACGGGGTCTCACTAGACTTCCTCCCACTTGCCAACATTGCCAACATTCTCAACTGCCAAAAAA 2873
CTCACAACACCACCTGGCAATTTGATTTTTTTTTTTTCAGAGACGGGGTCTCACTATGTTGCCAATCATGTTCACTGCAGTCTCCCACCTGAGTACCCCAGACTTCCTCCCACCTTGTTAGTTAGTAATAAAGCTTTCTCAACTGCCAAAAAA 2992
AAAAAAAAAAAAAAAAAAAAAA 3' 3023
```

```
              4                 13
ICAM-2    E V H V R P N K L A V S Q R - S L E V N C S T
mo ICAM-1 Q V S I H P R E A F L P Q G G S V Q V N C S S
hu ICAM-1 Q T S V S P S K V I L P R G G S V L V T C S T
          K A                   E A
            A G L               E

USE OF FUNCTIONAL DERIVATIVES OF THE INTERCELLULAR ADHESION MOLECULE ICAM-1 IN DIAGNOSIS OF VIRAL INFECTION

CROSS-REFERENCE TO RELATED APPLICATIONS

This application is a divisional of application Ser. No. 08/420,720, filed Apr. 11, 1995 (pending); which is a continuation of application Ser. No. 08/136,408, filed Oct. 15, 1993 (abandoned); which is a continuation of application Ser. No. 07/514,033, filed Apr. 27, 1990 (abandoned); which is a continuation-in-part of application Ser. No. 07/324,073, filed Mar. 16, 1989 (abandoned); which is a continuation-in-part of application Ser. No. 07/454,292, filed Dec. 22, 1989 (abandoned).

BACKGROUND OF THE INVENTION

1. Field of the Invention

The present invention relates to functional domains and fragments of the intercellular adhesion molecule, ICAM-1. Such functional domains and fragments may be used in the treatment of viral, and particularly rhinoviral disease.

2. Description of the Related Art

I. The Intercellular Adhesion Molecule ICAM-1 and Cellular Adhesion

The intercellular adhesion molecule ICAM-1 was first identified and partially characterized according to the procedure of Rothlein, R. et al. (*J. Immunol.* 137:1270–1274 (1986)), which reference is herein incorporated by reference. ICAM-1, its preparation, purification, and characteristics are disclosed in U.S. patent application Ser. No. 07/045,963 (filed on May 4, 1987), Ser. No. 07/115,798 (filed on Nov. 2, 1987), Ser. No. 07/155,943 (filed on Feb. 16, 1988), Ser. No. 07/189,815 (filed on May 3, 1988) and Ser. No. 07/250,446 (filed on Sep. 28, 1988), all of which applications are herein incorporated by reference in their entirety.

ICAM-1 was initially realized as being involved in the process of cellular adhesion between endothelial cells and leukocytes. Cellular adhesion is the process through which leukocytes attach to cellular substrates, such as endothelial cells, in order to migrate from circulation to sites of ongoing inflammation, and properly defend the host against foreign invaders such as bacteria or viruses. An excellent review of the defense system is provided by Eisen, H. W., (*In: Microbiology*, 3rd Ed., Harper & Row, Philadelphia, Pa. (1980), pp. 290–295 and 381–418).

One of the molecules on the surface of endothelial cells which participates in the adhesion process is ICAM-1. This molecule has been shown to mediate adhesion by binding to molecules of the CD-18 family of glycoproteins which are present on the cell surfaces of leukocytes (Sanchez-Madrid, F. et al., *J. Exper. Med.* 158:1785–1803 (1983); Keizer, G. D. et al., *Eur. J. Immunol.* 15:1142–1147 (1985)). This glycoprotein family is composed of heterodimers having one alpha chain and one beta chain. Although the alpha chain of each of the antigens differed from one another, the beta chain was found to be highly conserved (Sanchez-Madrid, F. et al., *J. Exper. Med.* 158:1785–1803 (1983)). The beta chain of the glycoprotein family (sometimes referred to as "CD18") was found to have a molecular weight of 95 kd whereas the alpha chains were found to vary from 150 kd to 180 kd (Springer, T., *Fed. Proc.* 44:2660–2663 (1985)). Although the alpha subunits of the membrane proteins do not share the extensive homology shared by the beta subunits, close analysis of the alpha subunits of the glycopro-teins has revealed that there are substantial similarities between them. There are three major members of the CO-18 family: p150,95, MAC-1 and LFA-1. Mac-1 is a heterodimer found on macrophages, granulocytes and large granular lymphocytes. LFA-1 is a heterodimer found on most lymphocytes (Springer, T. A., et al. *Immunol. Rev.* 68:111–135 (1982)). P150,95 has a tissue distribution similar to Mac-1, and also plays a role in cellular adhesion (Keizer, G. et al., *Eur. J. Immunol.* 15:1142–1147 (1985)). Reviews of the similarities between the alpha and beta subunits of the LFA-1 related glycoproteins are provided by Sanchez-Madrid, F. et al., (*J. Exper. Med.* 158:586–602 (1983); *J. Exper. Med.* 158:1785–1803 (1983)).

II. The Cellular Receptor for Human Rhinovirus

Abraham et al. (*J. Virol.* 51:340–345 (1984)) discovered that the majority of randomly selected human rhinovirus ("HRV") serotypes were able to bind to the same cellular receptor. A monoclonal antibody was subsequently developed by Colonno et al. (Colonno et al., *J. Cell. Biochem. Suppl.* 10 (part D):266 (1986); Colonno et al., *J. Virol.* 57:7–12 (1986); Colonno et al., European Patent Application Publication No. 169,146) which was capable of blocking attachment of HRV of the major serotype to the surfaces of endothelial cells. The endothelial cell receptor protein recognized by this antibody was isolated and found to be a 90 kd protein (Tomassini et al., *J. Virol.* 58:290–295 (1986).

SUMMARY OF THE INVENTION

The present invention relates to the use of functional derivatives of Intercellular Adhesion Molecule-1 (ICAM-1) in anti-viral therapy. Of particular concern to the invention are those functional derivatives of ICAM-1 which comprises fragments of the intact ICAM-1 molecule.

In detail, the invention provides a method for treating viral infection in an individual in need of such treatment, wherein the method comprises providing to the individual an amount of a fragment of ICAM-1 or a fragment of a functional derivative of ICAM-1 sufficient to suppress viral infection.

The invention further provides a method of diagnosing the presence of viral infection, the method comprising:
(a) incubating a biological sample suspected of containing a virus with a detectably labeled ICAM-1 functional derivative;
(b) determining whether any of the detectably labeled ICAM-1 functional derivative has become bound to virus.

The invention further provides a method of preventing viral infection which comprises providing to a recipient a vaccine composition, the composition containing a virus bound to a functional derivative of ICAM-1.

BRIEF DESCRIPTION OF THE FIGURES

FIGS. 1A–C show the nucleotide and amino acid sequence of ICAM-1 cDNA. The first ATG is at position 58. Translated sequences corresponding to ICAM-1 tryptic peptides are underlined. The hydrophobic putative signal peptide and transmembrane sequences have a bold underline. N-linked glycosylation sites are boxed. The polyadenylation signal AATAAA at position 2976 is overlined. The sequence shown is for the HL-60 cDNA clone. The endothelial cell cDNA was sequenced over most of its length and showed only minor differences.

FIG. 2 shows the ICAM-1 homologous domains and relationship to the immunoglobulin supergene family. (A) Alignment of 5 homologous domains (D1–5). Two or more identical residues which aligned are boxed. Residues conserved 2 or more times in NCAM domains, as well as resides conserved in domains of the sets C2 and C1 were aligned with the ICAM-1 internal repeats. The location of the predicted β strands in the ICAM-1 domain is marked with bars and lower case letters above the alignments, and the known location of β-strands in immunoglobulin C domains is marked with bars and capital letters below the alignment. The position of the putative disulfide bridge within ICAM-1 domains is indicated by S-S. (B-D) Alignment of protein domains homologous to ICAM-1 domains; proteins were initially aligned by searching NBRF databases using the FASTP program. The protein sequences are MAG, NCAM, T cell receptor α subunit V domain, IgMμ chain and α-1-B-glyco-protein.

FIG. 3 shows the alignment of ICAM amino-terminal domains.

DESCRIPTION OF THE PREFERRED EMBODIMENTS

I. Characteristics of ICAM-1

Figure 4:
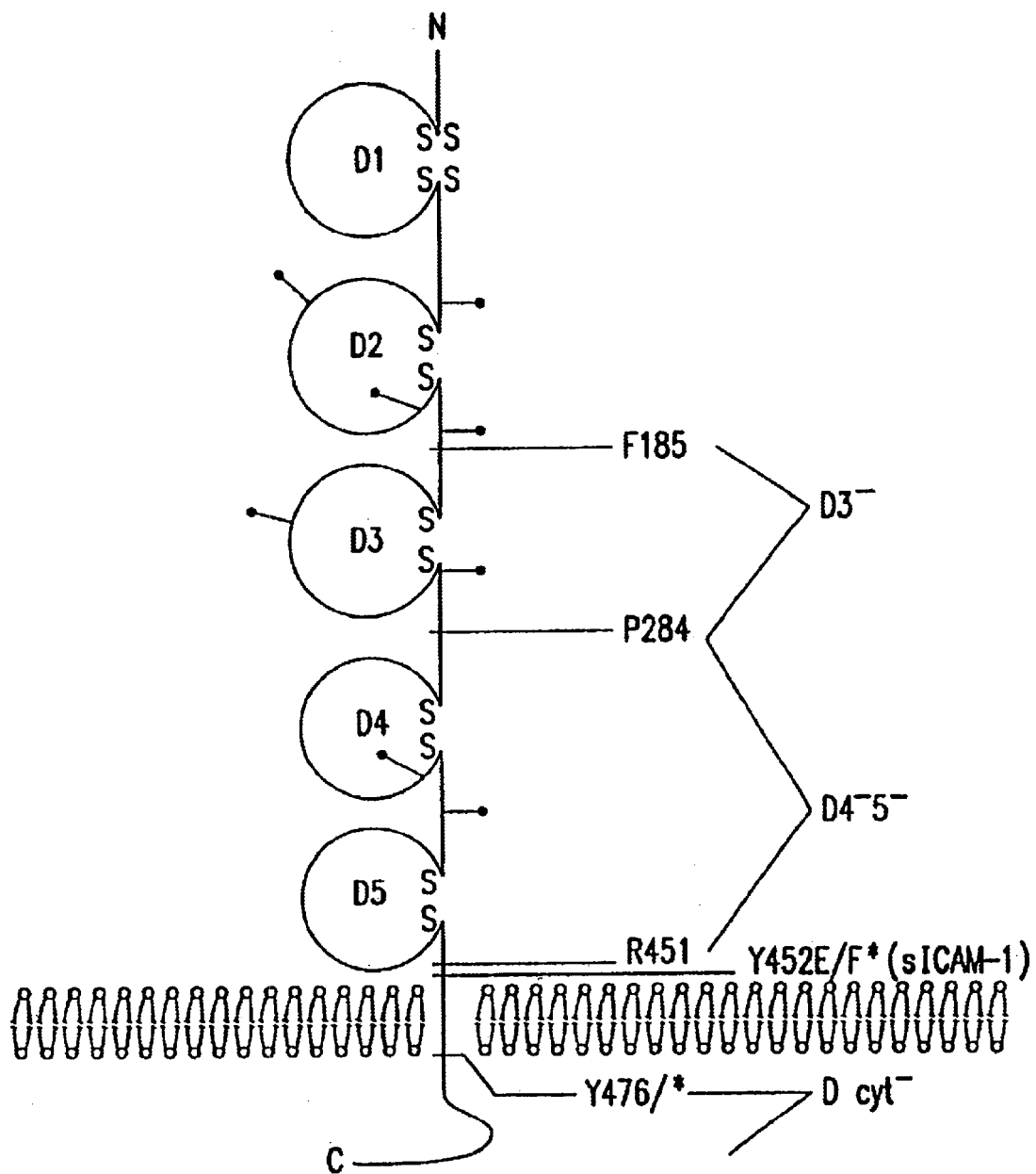
FIG. 4 shows an ICAM-1 schematic with position of domain deletions.
Figure 5A:
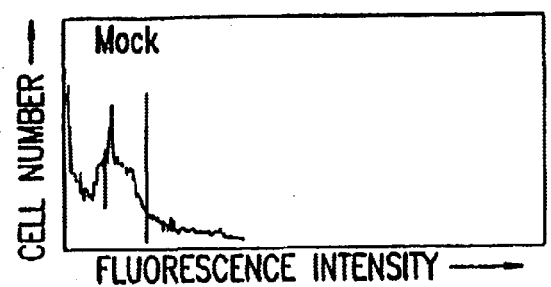
FIGS. 5A–E show the expression of ICAM-1 deletion mutants in COS cells. COS cells were analyzed by flow cytofluorometry following indirect immunofluorescence with RR1/1.
Figure 5B:
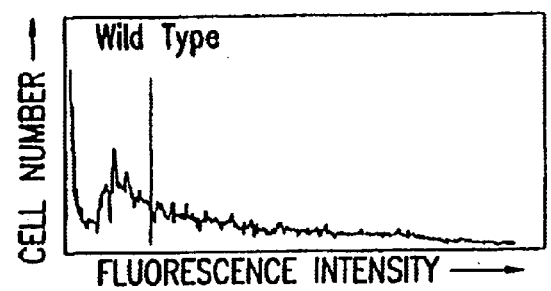
Figure 5C:
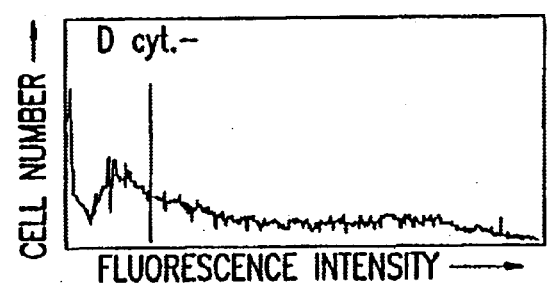
Figure 5D:
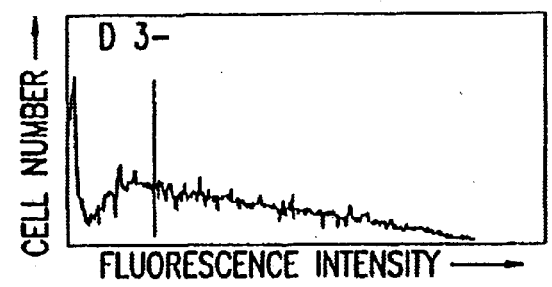
Figure 5E:
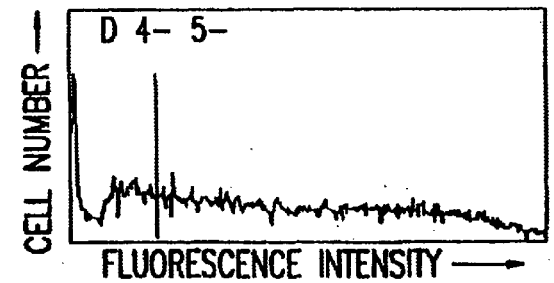

ICAM-1 displays molecular weight heterogeneity in different cell types with a molecular weight of 97 kd on fibroblasts, 114 kd on the myelomonocytic cell line U937, and 90 kd on the B lymphoblastoid cell JY. ICAM-1 biosynthesis has been found to involve an approximately 73 kd intracellular precursor. The non-N-glycosylated form resulting from tunicamycin treatment (which inhibits glycosylation) has a molecular weight of 55 kd. ICAM-1 has been designated "CD 54."

ICAM-1 isolated from phorbol ester stimulated U937 cells or from fibroblast cells yields an identical major product having a molecular weight of 60 kd after chemical deglycosylation. ICAM-1 monoclonal antibodies interfere with the adhesion of phytohemagglutinin blasts to LFA-1 deficient cell lines. Pretreatment of fibroblasts, but not lymphocytes, with monoclonal antibodies capable of binding ICAM-1 inhibits lymphocyte-fibroblast adhesion. Pretreatment of lymphocytes, but not fibroblasts, with antibodies against LFA-1 has also been found to inhibit lymphocyte-fibroblast adhesion.

ICAM-1 is, thus, the binding ligand of the CD 18 complex on leukocytes. It is inducible on fibroblasts and endothelial cells in vitro by inflammatory mediators such as IL-1, gamma interferon and tumor necrosis factor in a time frame consistent with the infiltration of lymphocytes into inflammatory lesions in vivo (Dustin, M. L., et. al., *J. Immunol* 137:245–254, (1986); Prober, J. S., et. al., *J. Immunol* 137:1893–1896, (1986)). Further ICAM-1 is expressed on non-hemato-poietic cells such as vascular endothelial cells, thymic epithelial cells, other epithelial cells, and fibroblasts and on hematopoietic cells such as tissue macophages, mitogen-stimulated T lymphocyte blasts, and germinal center B-cells and dendritic cells in tonsils, lymph nodes and Peyer's patches (Dustin, M. L., et. al., *J. Immunol* 137:245–254, (1986)).

ICAM-1 is expressed on keratinocytes in benign inflammatory lesions such as allergic eczema, lichen planus, exanthema, urticaria and bullous diseases. Allergic skin reactions provoked by the application of a hapten on the skin to which the patient is allergic also revealed a heavy ICAM-1 expression on the keratinocytes. On the other hand toxic patches on the skin did not reveal ICAM-1 expression on the keratinocytes.

ICAM-1 is present on keratinocytes from biopsies of skin lesions from various dermatological disorders and ICAM-1 expression is induced on lesions from allergic patch tests while keratinocytes from toxic patch test lesions failed to express ICAM-1.

Hydrophobicity analysis (Kyte, J., et al., *J. Molec. Biol.*, 157:105–132 (1982)) of ICAM-1 suggests the presence of a 27 residue signal sequence. The assignment of the +1 glutamine is consistent with our inability to obtain N-terminal sequence on 3 different ICAM-1 protein preparations; glutamine may cyclize to pyroglumatic acid, resulting in a blocked N-terminus. The translated sequence from 1 to 453 is predominantly hydrophilic followed by a 24 residue hydrophobic putative transmembrane domain. The transmembrane domain is immediately followed by several charged residues contained within a 27 residue putative cytoplasmic domain.

The predicted size of the mature polypeptide chain is 55,219 daltons, in excellent agreement with the observed size of 55,000 for deglycosylated ICAM-1 (Dustin, M. L., et al., *J. Immunol.* 137:245–254 (1986)). Eight N-linked glycosylation sites are predicted. Absence of asparagine in the tryptic peptide sequences of 2 of these sites confirm their glycosylation and their extracellular orientation. Assuming 2,500 daltons per high mannose N-linked carbohydrate, a size of 75,000 daltons is predicted for the ICAM-1 precursor, compared to the observed six of 73,000 daltons (Dustin, M. L., et al., *J. Immunol.* 137:245–254 (1986)). After conversion of high mannose to complex carbohydrate, the mature ICAM-1 glycoprotein is 76 to 114 kd, depending on cell type (Dustin, M. L., et al., *J. Immunol.* 137:245–254 (1986)). Thus ICAM-1 is a heavily glycosylated but otherwise typical integral membrane protein.

ICAM-1 is, therefore, a cellular substrate to which lymphocytes can attach, so that the lymphocytes may migrate to sites of inflammation and/or carry out various effector functions contributing to this inflammation. Such functions include the production of antibody, lysis of virally infected target cells, etc.

II. Anti-viral Functional Derivatives of ICAM-1

One aspect of the present invention relates to the discovery of that ICAM-1 is the cellular receptor of certain viruses, and is thus required in order for the virus to adhere to and infect human cells (Greve, J. M. et al., *Cell* 56:839–847 (1989); Staunton, D. E. et al., *Cell* 56:849–853 (1989), both of which references are incorporated by reference herein in their entirety). In particular, rhinoviruses, and especially rhinoviruses of the major serotype have been found to be capable of mediating their infection through their capacity to bind to the ICAM-1 molecules present on cell surfaces.

The present invention is directed toward the use of functional derivatives of ICAM-1 to treat viral infection. Because such derivatives are capable of competing with the ICAM-1 of endothelial cells for viral attachment, their administration to a recipient individual results in the adsorption of virus, and thus decreases the percentage of viruses which attach and infect the cells of an infected individual.

As used herein, a "functional derivative" of ICAM-1 is a compound which possesses the capacity to be recognized by, and to become associated with (i.e. to bind, complex with, etc.) a virus. In addition to such biological function, a functional derivative of ICAM-1 has a structure which is substantially similar to a structure of a "fragment," "variant," "analog," "chemical derivative," or "peptidomimetic" of ICAM-1. A molecule is said to be "substantially similar" to another molecule if both molecules have substantially similar structures or if both molecules possess a similar biological activity. A "fragment" of a molecule such as ICAM-1, is meant to refer to any polypeptide subset of the molecule. Of particular concern to the present invention are functional derivatives of ICAM-1 which are composed of one or more fragments of ICAM-1 (such fragments may or may not be contiguous in the intact ICAM-1 molecule). Soluble (i.e not membrane bound) functional derivatives are especially preferred.

A "variant" of a molecule such as ICAM-1 is meant to refer to a molecule substantially similar in structure and function to either the entire molecule, or to a fragment thereof. Thus, as the term variant is used herein, two molecules are variants of one another if they possess a similar activity even if the structure of one of the molecules is not found in the other, or if the sequence of amino acid residues is not identical. Mutant molecules of ICAM-1 are an example of ICAM-1 variants.

An "analog" of a molecule such as ICAM-1 is meant to refer to a molecule substantially similar in function to either the entire molecule or to a fragment thereof.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). "Antigen-derivatized" molecules constitute a special class of "chemical derivatives." An "adjuvant-derivatized" molecule is a molecule (such as a functional derivative of ICAM-1) which contains an adjuvant moiety. The binding of such a molecule to a virus brings the antigen moiety into close proximity with the virus and thereby increases the immunogenicity of the virus, and promotes anti-viral therapy. Any suitable adjuvant moiety may be employed; however, it is preferable to employ an adjuvant such as, for example, muramyl dipeptide (Allison, A. C. et al., *UCLA SymR. Molec. Cell. Biol., New Ser.* 84:401–410 (1988); Riveau, G. et al., *J. Lymph. Res.* 44:448–454 (1988)). Procedures for coupling such moieties to a molecule are well known in the art.

A "peptidomimetic" of ICAM-1 is a compound whose tertiary structure is substantially similar to the tertiary structure of ICAM-1.

The anti-viral agents of the present invention may-be obtained by natural processes (such as, for example, by inducing an animal, plant, fungi, bacteria, etc., to produce an analog of ICAM-1, or by inducing an animal to produce polyclonal or monoclonal anti-ICAM-1 anti-idiotypic); by synthetic methods (such as, for example, by using the Merrifield method for synthesizing polypeptides of a functional derivatives of ICAM-1, etc.); or by recombinant technology (such as, for example, to produce the anti-viral functional derivatives of ICAM-1 in diverse hosts (i.e., yeast, bacteria, fungi, cultured mammalian cells, etc.), or from recombinant plasmids or viral vectors), or by proteolysis. The choice of which method to employ will depend upon factors such as convenience, desired yield, etc. It is not necessary to employ only one of the above-described methods, processes, or technologies to produce a particular anti-viral agent; the above-described processes, methods, and technologies may be combined in order to obtain a particular anti-viral agent.

Functional derivatives of ICAM-1 having up to about 100 residues may be conveniently prepared by in vitro synthesis. If desired, such fragments may be modified by reacting targeted amino acid residues of the purified or crude protein with an organic derivatizing agent that is capable of reacting with selected side chains or terminal residues. The resulting covalent derivatives may be used to identify residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitro-phenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also-is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methyl-issurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form 0-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R'-N-C-N-R'),such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking an ICAM-1 functional derivative molecule to a water-insoluble support matrix or surface for use in the method for cleaving an ICAM-1 functional derivatives fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195, 128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Functional derivatives of ICAM-1 having altered amino acid sequences can also be prepared by mutations in the DNA. The nucleotide sequence which encodes the ICAM-1 gene is shown in FIG. 1. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these functional derivatives ordinarily are prepared by site-directed mutagenesis of nucleotides in the DNA encoding the ICAM-1 molecule, thereby producing DNA encoding the functional derivative, and thereafter expressing the DNA in recombinant cell culture. The functional derivatives typically exhibit the same qualitative biological activity as the naturally occurring analog. They may, however, differ substantially in such characteristics with respect to the normally produced ICAM-1 molecule.

While the site for introducing an amino acid sequence variation is predetermined, the mutation per se need not be predetermined. For example, to optimize the performance of a mutation at a given site, random mutagenesis may be conducted at the target codon or region and the expressed ICAM-1 functional derivatives screened for the optimal combination of desired activity. Techniques for making substitution mutations at predetermined sites in DNA having a known sequence are well known, for example, site-specific mutagenesis.

Preparation of an ICAM-1 functional derivative molecule in accordance herewith is preferably achieved by site-specific mutagenesis of DNA that encodes an earlier prepared functional derivatives or a nonvariant version of the protein. Site-specific mutagenesis allows the production of ICAM-1 functional derivatives through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macro-molecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as JM101 cells, and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete ICAM-1 molecule sequence) may range generally from about 1 to 10 residues, more preferably 1 to 5. An example of a terminal insertion includes a fusion of a signal sequence, whether heterologous or homologous to the host cell, to the N-terminus of the molecule to facilitate the secretion of the ICAM-1 functional derivative from recombinant hosts.

The third group of functional derivatives are those in which at least one amino acid residue in the ICAM-1 molecule, and preferably, only one, has been removed and a different residue inserted in its place. Such substitutions preferably are made in accordance with the following Table when it is desired to modulate finely the characteristics of the ICAM-1 molecule.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the ICAM-1 molecule. However, when it is difficult to predict the exact effect of the substitution, deletion, or insertion in advance of doing so, one skilled in the art will appreciate that the effect will be evaluated by routine screening assays. For example, a functional derivative typically is made by site-specific mutagenesis of the native ICAM-1 molecule-encoding nucleic acid, expression of the variant nucleic acid in recombinant cell culture, and, optionally, purification from the cell culture, for example, by immunoaffinity adsorption on an anti-ICAM-1 molecule antibody column (to absorb the functional derivative by binding it to at least one remaining immune epitope).

The activity of the cell lysate or purified ICAM-1 molecule functional derivative is then screened in a suitable screening assay for the desired characteristic. For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

III. Mapping of ICAM-1 Functional Domains

Studies of ICAM-1 have revealed that the molecule possesses 7 domains. Five of these domains are extracellular (domain 5 being closest to the cell surface, domain 1 being furthest from the cell surface), one domain is a transmembrane domain, and one domain is cytoplasmic (i.e. lies within the cell). In order to determine which domains contribute to the ability of ICAM-1 to bind virus, epitope mapping studies may be used. To conduct such studies, different deletion mutants are prepared and characterized for their capacity to bind to virus. Any virus capable of binding to ICAM-1 may be employed for such studies, however, it is preferable to use human rhinovirus of the major serotype (HRV-14). Alternatively, the studies may be accomplished using anti-ICAM antibody known to interfere with the capacity of ICAM-1 to bind virus or LFA-1. Examples of such suitable antibody include RR1/1 (Rothlein, R. et al., *J. Immunol.* 137:1270–1274 (1986)), R6.5 (Springer, T. A. et al., U.S. patent application Ser. No. 07/250,446), LB-2 (Clark, E. A. et al., In: *Leukocyte Typing I* (A. Bernard, et al., Eds.), Springer-Verlag pp 339–346 (1984)), or CL203 (Staunton, D. E. et al., *Cell* 56:849–853 (1989)). In yet another alternative, such studies may be accomplished by determining whether the deletion mutants are capable of binding to LFA-1. Methods which may be readily adapted to permit the performance of such experiments are disclosed in European Patent Application Publication No. 169,146, in U.S. patent application Ser. No. 07/045,963, and in Rothlein, R. et al. (*J. Immunol.* 137:1270–1274 (1986)), all of which references are herein incorporated by reference.

Deletion mutants of ICAM-1 can be created by any of a variety of means. It is, however, preferable to produce such mutants via site directed mutagenesis, or by other recombinant means (such as by constructing ICAM-1 expressing gene sequences in which sequences that encode particular protein regions have been deleted. Procedures which may be adapted to produce such mutants are well known in the art. Using such procedures, three ICAM-1 deletion mutants were prepared. The first mutant lacks amino acid residues F185 through P284 (i.e. deletion of domain 3). The second mutant lacks amino acid residues P284 through R451 (i.e. deletion of domains 4 and 5). The third mutant lacks amino acid residues after Y476 (i.e. deletion of cytoplasmic domain). The results of such studies indicate that domains 1, 2, and 3 are predominantly involved in ICAM-1 interactions with anti-ICAM-1 antibody, LFA-1 and virus.

IV. Effect of Mutations in ICAM-1 on Viral Binding

ICAM-1 has the ability to interact with and bind to viruses, and in particular, rhinoviruses of the major serotype within the genus Picornaviridae, group A coxsackieviruses (Colonno, R. J. et al., *J. virol.* 57:7–12 (1986)) and Mengo viruses (Rossmann, M. G. et al., *Virol.* 164:373–382 (1988)). This interaction is mediated by ICAM-1 amino acid residues which are present in domain 1 of the ICAM-1 molecule (FIGS. 1 and 2). Such interactions are assisted, however, by contributions from amino acids present in domains 2 and 3 of ICAM-1. Thus, among the preferred functional derivatives of the present invention are soluble fragments of the ICAM-1 molecule which contain domains& 1, 2, and 3 of ICAM-1. More preferred are soluble fragments of the ICAM-1 molecule which contain domains 1 and 2 of ICAM-1. Most preferred are soluble fragments of the ICAM-1 molecule which contain domain 1 of ICAM-1.

The soluble derivatives referred to above are derivatives which are not bound to a membrane of a cell. Such derivatives may comprise truncated molecules which lack a transmembrane domain. Alternatively, they may comprise mutant forms of the natural molecules which lack the capacity to be bound (or stably bound) to the membrane of a cell even though they contain a transmembrane domain. Soluble derivatives of ICAM-1 and their preparation are disclosed by Marlin, S. D. et al., *Nature* 344:70–72 (1990), which reference is incorporated herein by reference).

Several amino acid residues within the first ICAM-1 domain are involved in the interaction of ICAM-1 and, for example, human rhinoviruses of the major serotype. Substitutions of these amino acids with other amino acids alter the ability of such rhinoviruses to bind to ICAM-1. The natural amino acid residues and the effect of substitutions of these residues on the ability of the resulting mutant ICAM-1 molecule to bind to LFA-1, or to rhinovirus, or to anti-ICAM-1 monoclonal antibodies is shown in Table 3. In Table 3, residues are described with reference to the one letter code for amino acids, followed by the position of the residue in the ICAM-1 molecule. Thus, for example, "E90" refers to the glutamic acid residue at position 90 of ICAM-1. Similarly, "E90V" refers to the dipeptide composed of the glutamic acid residue at position 90 and the valine residue at position 91. The substitution sequence is indicated to the right of the slash ("/") mark. The Q1T, R13, Q27, K39KE, G46NN, R49KV, Q58, D71, K77T, and R166PQ residues of ICAM-1, for example, are involved in viral binding (Table 3).

Of particular interest to the present invention are functional derivatives of ICAM-1 which contain mutations in the ICAM-1 amino acids which are involved in viral binding. For example, replacement of V4 with G results in the formation of a mutant ICAM-1 molecule which is less able to bind to either rhinovirus or LFA-1 (Table 3). Replacement of the R13 residue of ICAM-1 with E leads to the formation of a mutant molecule with substantially less capacity to bind either LFA-1 or rhinovirus (Table 3). Replacement of the Q58 residue of ICAM-1 with H leads to the formation of a mutant molecule having a substantially normal capacity to bind LFA-1, but a substantially impaired capacity to bind rhinovirus (Table 3). Replacement of the D60S residues of ICAM-1 with KL leads to the formation of a mutant molecule having substantially less capacity to bind LFA-1, and having less capacity to bind rhinovirus (Table 3).

Functional derivatives of ICAM-1 which exhibit a decreased capacity to bind LFA-1, but retain a normal capacity to bind virus are especially preferred. Replacement of Q27 with L results in the formation of such a mutant ICAM-1 molecule. This ICAM-1 functional derivative has substantially less capacity to bind LFA-1 but retains a normal capacity to bind rhinovirus (Table 3). As seen in Table 3, several functional derivatives of ICAM-1 have been found to exhibit this preferred property. ICAM-1 functional derivatives having the following amino acid(s) at the indicated position: A3GL, L27, A34, H73, and T73 are examples of such preferred derivatives. The administration of such mutant molecules to a recipient would thus be capable of treating viral infection without altering natural ICAM-1-LFA-1 interactions. Hence such administration would permit treatment for viral infection, but not result in immunosuppression or interfere with inflammatory response in the recipient.

Glycosylation sites in the first and second domains are also involved in viral binding (Table 3). Replacement of N48 with H, or N175 with A, results in the formation of a mutant ICAM-1 molecule which is less capable of binding either virus or LFA-1. Replacement of N118 with Q, or N156 with E, results in the formation of a mutant ICAM-1 molecule which is less capable of binding LFA-1. In contrast, replacement of N103 with K, or N175TSA with QTLG, results in the formation of a mutant ICAM-1 molecule which is substantially incapable of binding either virus or LFA-1. cl V. Anti-viral Agents of the Present Invention In addition to the above-described functional derivatives of ICAM-1, other agents which may be used in accordance of the present invention in the treatment of viral infection include antibody to ICAM-1, anti-idiotypic antibodies to anti-ICAM-1 antibodies, and receptor molecules (such as LFA-1, p150,95, Mac-1, etc.), or fragments of such molecules, which are capable of binding to ICAM-1.

The antibodies to ICAM-1 (or functional derivatives of ICAM-1) which may be employed may be either polyclonal or monoclonal.

The anti-idiotypic antibodies of interest to the present invention are capable of binding to HRV in competition with (or to the exclusion of) ICAM-1. Such antibodies can be obtained, for example, by raising antibody to an anti-ICAM-1 antibody, and then screening the antibody for the ability to bind HRV or a member of the CD 18 family such as LFA-1.

As indicated above, both polyclonal and monoclonal antibodies may be employed in accordance with the present invention. Of special interest to the present invention are antibodies to ICAM-1 (or their functional derivatives), or to members of the CD18 family (or their functional derivatives), which, are produced in humans, or are "humanized" (i.e. non-immunogenic in a human) by recombinant or other technology. Such antibodies are the equivalents of the monoclonal and polyclonal antibodies disclosed herein, but are less immunogenic, and are better tolerated by the patient.

Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041–1043 (1988); Liu, A. Y. et al., Proc. Natl. Acad. Sci. USA 84:3439–3443 (1987); Liu, A. Y. et al., J. Immunol. 139:3521–3526 (1987); Sun, L. K. et al., Proc. Natl. Acad. Sci. USA 84:214–218 (1987); Nishimura, Y. et al., Canc. Res. 47:999–1005 (1987); Wood, C. R. et al., Nature 314:446–449 (1985)); Shaw et al., J. Natl.Cancer Inst. 80:1553–1559 (1988); all of which references are incorporated herein by reference). General reviews of "humanized" chimeric antibodies are provided by Morrison, S. L. (Science, 229:1202–1207 (1985)) and by Oi, V. T. et al., BioTechnigues 4:214 (1986); which references are incorporated herein by reference).

Suitable "humanized" antibodies can be alternatively produced by CDR or CEA substitution (Jones, P. T. et al., Nature 321:552–525 (1986); Verhoeyan et al., Science 239:1534 (1988); Beidler, C. B. et al., J. Immunol. 141:4053–4060 (1988); all of which references are incorporated herein by reference).

Since molecules of the CD-18 family are able to bind to ICAM-1, administration of such molecules (for example as heterodimers having both alpha and beta subunits, or as molecules composed of only an alpha, or a beta subunit, or as molecules having fragments of either or both subunits) is able to compete with (or exclude) HRV for binding to ICAM-1 present on endothelial cells.

VI. Therapeutic Uses of the Invention

The therapeutic effects of the invention may be obtained by providing to a patient a therapeutically active functional derivative of ICAM-1, a member of the CD18 family capable of binding to ICAM-1, an anti-idiotypic antibody to anti-ICAM antibody, or an antibody to ICAM-1. The therapeutic advantages of such functional derivatives may be augmented through the use of functional derivatives of-ICAM-1 possessing additional amino acid residues added to enhance coupling to carrier or to enhance the anti-viral activity of the ICAM-1 functional derivative. The scope of the present invention is further intended to include functional derivatives of ICAM-1 which lack certain amino acid residues, or which contain altered amino acid residues, so long as such derivatives exhibit the capacity to bind virus.

The ICAM-1 functional derivatives disclosed herein are said to be "substantially free of natural contaminants" if preparations which contain them are substantially free of materials with which these products are normally and naturally found.

In providing a patient with any of the therapeutically active molecules of the present invention, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered.

The therapeutic agents of the present invention may be administered to patients intravenously, intramuscularly, subcutaneously, enterally, or parenterally. When administering such agents by injection, the administration may be by continuous infusion, or by single or multiple boluses. An especially preferred means of administration is by intranasal administration.

The anti-viral agent may be provided to a recipient as part of a "pharmacologically acceptable" composition. A composition is said to be "pharmacologically acceptable" if its administration can be tolerated by a recipient patient. The anti-viral agents of the present invention are intended to be provided to recipient subjects in a "therapeutically active" amount. An amount is said to be "therapeutically active" if the amount administered is physiologically significant. An agent is physiologically significant if its presence results in a detectable change in the physiology of a recipient patient. An amount of agent is "therapeutically active," for example, when its administration to a recipient patient is capable of suppressing or attenuating viral infection or infectivity in that recipient.

The administration of the anti-viral agents of the present invention may be for either a "prophylactic" or "therapeutic" purpose. When provided prophylactically, the anti-viral agent is provided in advance of any symptom of viral infection (for example, prior to, at, or shortly after the time of infection, but in advance of any symptoms of such infection). The prophylactic administration of the agent serves to prevent or attenuate any subsequent viral infection, or to reduce the possibility that such infection will be contagious to others.

When provided therapeutically, the anti-viral agent is provided at (or shortly after) the onset of a symptom of actual viral infection (such as, for example, nasal congestion, fever, etc. The therapeutic administration of the agent serves to attenuate any actual viral infection.

The anti-viral agents of the present invention may, thus, be provided either prior to the onset of viral infection (so as to suppress an anticipated infection) or after the initiation of such infection.

The anti-viral molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of agent together with a suitable amount of carrier vehicle.

Additional pharmaceutical methods may be employed to control the duration of action. Control release preparations may be achieved through the use of polymers to complex or absorb the agent. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the anti-viral agent into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

VII. Diagnostic and Prognostic Uses of the Invention

The capacity of ICAM-1 to recognize and bind to human rhinovirus of the major serotype provides the basis for its use to diagnose the presence of a rhinovirus infection in an individual. At present, approximately 20% of all physician office visits in the United States involve complaints of symptoms which can be caused by either rhinovirus or bacterial infection. Since bacterial infection are treatable with antibiotics, but such agents are ineffective against rhinovirus, a means for distinguishing between rhinovirus and bacterial infection is highly desirable.

In accordance with the present invention, an assay capable of identifying the presence of rhinovirus in the mucus, nasal secretions, or other body fluids of an individual is provided. The human rhinovirus possesses 60 ICAM-1 binding sites, and is thus able to simultaneously bind 60 different ICAM-1 molecules. Each binding site is too small to be accessible to antibody.

In one embodiment, the assay would comprise incubating an amount of a detectably labeled ICAM-1 functional derivative molecules in the presence of a patient's mucus, nasal secretions, etc. and determining the amount of labeled molecule bound to the virus.

In a preferred embodiment, an unlabeled ICAM-1 functional derivative would be bound to a solid support (such as glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to a virus. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.glass, polystyrene, paper, cellulose, etc.).

The sample of fluid suspected of containing virus would be placed in contact with the bound ICAM-1 functional derivative, under conditions sufficient to permit virus which may be present in such fluid to bind to the support-bound ICAM-1 functional derivative. The support is then incubated in the presence of a labeled ICAM-1 functional derivative under conditions sufficient to permit the labeled ICAM-1 functional derivative to bind to an open ICAM-1 binding site on the virus. After washing away unbound molecules of the labeled ICAM-1 functional derivative, the amount of label bound to the support is determined. The presence of molecules of labeled ICAM-1 functional derivative bound to the support indicates the presence of virus in the fluid sample.

As will be readily perceived, any of a large number of equivalent assays may be alternatively employed without departing from the spirit of the above-described assay. For example, the assay can be conducted in liquid phase rather than through the use of a solid support. Alternatively, other variations of immunoassays can be employed. In lieu of using bound ICAM-1, one could employ bound anti-rhinovirus antibody. Such an assay would permit identification of the subserotype (or subspecies of the virus) depending upon the nature and specificity of the bound antibody.

Examples of types of labels which can be used in accordance with this aspect of the present invention include, but are not limited to, enzyme labels, radioisotopic labels, non-radioactive isotopic labels, fluorescent labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc.

Examples of suitable non-radioactive isotopic labels include $^{157}Gd$, $^{55}Mn$, $^{162}Dy$, $^{52}Tr$, $^{56}Fe$, etc.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to ICAM-1 functional derivatives can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

In addition to the above-described in vitro assays, it is possible to administer detectably labeled ICAM-1 functional derivatives to an individual in order to identify foci of infection by in vivo imaging. In yet another embodiment, samples of a patient's tissue could be removed and incubated in the presence of detectably labeled ICAM-1 functional derivatives in order to perform an in situ determination of viral infection. Such in situ analysis could also be performed on cells in culture, or on culture medium, in order to assess viral presence.

VIII. Use of the Anti-viral Agents of the Invention as a Vaccine

The present invention further provides a means for preventing viral infection through the preparation of a vaccine. In accordance with one embodiment of the invention, one or more rhinovirus subserotypes or subspecies (all of the major serotype) are incubated in the presence of a functional derivative of ICAM-1 in order to decrease the infectivity of the virus. The virus containing the bound ICAM-1 functional derivative is then administered to a patient (either by injection, orally, or intranasally) in an amount sufficient to provoke an immune response in the individual. Since the virus' ICAM-1 binding sites are blocked by the ICAM-1 functional derivative, no disease results from such administration.

In a preferred embodiment, the functional derivative of ICAM-1 employed to attenuate viral infectivity will be an adjuvant derivatized ICAM-1 molecule. The use of such a molecule serves to increase the immunogenicity of the attenuated virus.

Having now generally described the invention, the same will be more readily understood through reference to the following examples which are provided by way of illustration, and are not intended to be limiting of the present invention, unless-specified.

EXAMPLE 1

ICAM-1 is an Integrin-binding Member of the Immunoglobulin Supergene Family Alignment of ICAM-1 internal repeats was performed using the Microgenie protein alignment program (Queen, C., et al., *Nucl. Acid Res.*, 12:581–599 (1984)) followed by inspection. Alignment of ICAM-1 to IgM, N-CAM and MAG was carried out using Microgenie and the ALIGN program (Dayhoff, M. O., et al., *Meth. Enzymol.* 91:524–545 (1983)). Four protein sequence databases, maintained by the National Biomedical Research Foundation, were searched for protein sequence similarities using the FASTP program of Williams and Pearson (Lipman, D. J., et al., *Science* 227:1435–1439 (1985)).

Since ICAM-1 is a ligand of an integrin, it was unexpected that it would be a member of the immunoglobulin supergene family. However, inspection of the ICAM-1 sequence shows that it fulfills all criteria proposed for membership in the immunoglobulin supergene family. These criteria are discussed in turn below.

The entire extracellular domain of ICAM-1 is constructed from 5 homologous immunoglobulin-like domains which are shown aligned in FIG. 2A. Domains 1–4 are 88, 97, 99, and 99 residues long, respectively and thus are of typical Ig domain size; domain 5 is truncated within 68 residues. Searches of the NBRF data base using the FASTP program revealed significant homologies with members of the immunoglobulin supergene family including IgM and IgG C domains, T cell receptor α subunit variable domain, and alpha 1 beta glycoprotein (FIGS. 2B–D).

Using the above information, the amino acid sequence of ICAM-1 was compared with the amino acid sequences of other members of the immunoglobulin supergene family.

Three types of Ig superfamily domains, V, C1, and C2 have been differentiated. Both V and C domains are constructed from 2 β-sheets linked together by the intradomain disulfide bond; V domains contain 9 anti-parallel β-strands while C domains have 7. Constant domains were divided into the C1- and C2-sets based on characteristic residues shown in FIG. 2A. The C1-set includes proteins involved in antigen recognition. The C2-set includes several Fc receptors and proteins involved in cell adhesion including CD2, LFA-3, MAG, and NCAM. ICAM-1 domains were found to be most strongly homologous with domains of the C2-set placing ICAM-1 in this set; this is reflected in stronger similarity to conserved residues in C2 than C1 domains as shown for β-strands B–F in FIG. 2. Also, ICAM-1 domains aligned much better with β-strands A and G of C2 domains than with these strands in V and C1 domains, allowing good alignments across the entire C2 domain strength. Alignments with C2 domains from NCAM, MAG, and alpha 1-β glycoprotein are shown in FIGS. 2B and 2C; identity ranged from 28 to 33%. Alignments with a T cell receptor Vα 27% identity and IgM C domain 3 34% identity are also shown (FIGS. 2B, 2D).

One of the most important characteristics of immunoglobulin domains is the disulfide-bonded cysteines bridging the B and F β strands which stabilizes the β sheet sandwich; in ICAM-1 the cysteines are conserved in all cases except in strand f of domain 4 where a leucine is found which may face into the sandwich and stabilize the contact as proposed for some other V- and C2-sets domains. The distance between the cysteines (43, 50, 52, and 37 residues) is as described for the C2-set.

To test for the presence of intrachain disulfide bonds in ICAM-1, endothelial cell ICAM-1 was subjected to SDS-PAGE under reducing and non-reducing conditions. Endothelial cell ICAM-1 was used because it shows less glycosylation heterogeneity than JY or hairy cell splenic ICAM-1 and allows greater sensitivity to shifts in $M_r$. ICAM-1 was, therefore, purified from 16 hour LPS (5 μg/ml) stimulated umbilical vein endothelial cell cultures by immunoaffinity chromatography as described above. Acetone precipitated ICAM-1 was resuspended in sample buffer (Laemmli, U. K., *Nature* 227:680–685 (1970)) with 0.25% 2-mercaptoethanol or 25 mM iodoacetamide and brought to 100° C. for 5 min. The samples were subjected to SDS-PAGE 4670 and silver staining 4613. Endothelial cell ICAM-1 had an apparent $M_r$ of 100 Kd under reducing conditions and 96 Kd under non-reducing conditions strongly suggesting the presence of intrachain disulfides in native ICAM-1.

Use of the primary sequence to predict secondary structure (Chou, P. Y., et al., *Biochem.* 13:211–245 (1974)) showed the 7 expected β-strands in each ICAM-1 domain, labeled a-g in FIG. 2A upper, exactly fulfilling the prediction for an immunoglobulin domain and corresponding to the positions of strands A–H in immunoglobulins (FIG. 2A, lower). Domain 5 lacks the A and C strands but since these form edges of the sheets the sheets could still form, perhaps with strand D taking the place of strand C as proposed for some other C2 domains; and the characteristic disulfide bond between the B and F strands would be unaffected. Thus, the criteria for domain size, sequence homology, conserve cysteines forming the putative intradomain disulfide bond, presence of disulfide bonds, and predicted β sheet structure are all met for inclusion of ICAM-1 in the immunoglobulin supergene family.

ICAM-1 was found to be most strongly homologous with the NCAM and MAG glycoproteins of the C2 set. This is of particular interest since both NCAM and MAG mediate cell-cell adhesion. NCAM is important in neuron-neuron and neuro-muscular interactions (Cunningham, B. A., et al., Science 236:799–806 (1987)), while MAG is important in neuron-oligodendrocyte and oligodendrocyte-oligodendrocyte interactions during myelination (Poltorak, M., et al., J. Cell Biol. 105:1893–1899 (1987)). The cell surface expression of NCAM and MAG is developmentally regulated during nervous system formation and myelination, respectively, in analogy to the regulated induction of ICAM-1 in inflammation (Springer, T. A., et al., Ann. Rev. Immunol. 5:223–252 (1987)). ICAM-1, NCAM (Cunningham, B. A., et al., Science 236:799–806 (1987)), and MAG (Salzer, J. L., et al., J. Cell. Biol. 104:957–965 (1987)) are similar in overall structure as well as homologous, since each is an integral membrane glycoprotein constructed from 5 C2 domains forming the N-terminal extracellular region, although in NCAM some additional non-Ig-like sequence is present between the last C2 domain and the transmembrane domain. ICAM-1 aligns over its entire length including the transmembrane and cytoplasmic domains with MAG with 21% identity; the same % identity is found comparing the 5 domains of ICAM-1 and NCAM-1. The CDNA sequence of ICAM-1 is shown in FIG. 1. Domain by domain comparisons show that the level of homology between domains within the ICAM-1 and NCAM molecules (x±s.d. 21±2.8% and 18.6±3.8%, respectively) is the same as the level of homology comparing ICAM-1 domains to NCAM and MAG domains (20.4±3.7 and 21.9±2.7, respectively). Although there is evidence for alternative splicing in the C-terminal regions of NCAM (Cunningham, B. A., et al., Science 236:799–806 (1987); Barthels, D., et al., EMBO J. 6:907–914 (1987)) and MAG (Lai, C., et al., Proc. Natl. Acad. Sci. (USA) 84:4377–4341 (1987)), no evidence for this has been found in the sequencing of endothelial or HL-60 ICAM-1 clones or in studies on the ICAM-1 protein backbone and precursor in a variety of cell types (Dustin, M. L., et al., J. Immunol. 137:245–254 (1986)).

EXAMPLE 2

Genetic Construction and Expression of Truncated Derivatives of ICAM-1

In its natural state, ICAM-1 is a cell membrane-bound protein containing an extracellular region of 5 immunoglobulin-like domains, a transmembrane domain, and a cytoplasmic domain. It was desirable to construct functional derivatives of ICAM-1 lacking the transmembrane domain and/or the cytoplasmic domain in that a soluble, secreted form of ICAM-1 could be generated. These functional derivatives were constructed by oligonucleotide-directed mutagenesis of the ICAM-1 gene, followed by expression in monkey cells after transfection with the mutant gene.

Mutations in the ICAM-1 gene resulting in amino acid substitutions and/or truncated derivatives were generated by the method of Kunkel, T., (Proc. Natl. Acad. Sci. (U.S.A.) 82:488–492 (1985)). ICAM-1 cDNA prepared as described above was digested with restriction endonucleases Sal1 and Kpn1, and the resulting 1.8 kb DNA fragment was subcloned into the plasmid vector CDM8 (Seed, B. et al., Proc. Natl. Acad. Sci. (U.S.A.) 84:3365–3369 (1987)). A dut⁻, ung⁻ strain of E. coli (BW313/P3) was then transformed with this construct, designated pCD1.8C. A single-strand uracil-containing template was rescued from the transformants by infection with the helper phage R408 (Stratagene$^R$). Mutant ICAM-1 cDNAs were then generated by priming a second strand synthesis with an oligonucleotide possessing mismatched bases, and subsequent transformation of a unq⁺ host (MC1061/P3) with the resulting heteroduplex. Mutants were isolated by screening for newly created endonuclease restriction sites introduced by the mutant oligonucleotide. The mutant ICAM-1 protein was expressed by transfection of Cos-7 cells with the mutant DNA in the eukaryotic expression vector CDM8 using standard DEAE-Dextran procedures (Selden, R. F. et al., In: Current Protocols in Molecular Biology (Ausubel, F. M. et al., eds.) pages 9.2.1–9.2.6 (1987)).

A truncated functional derivative of ICAM-1 lacking the transmembrane and cytoplasmic domains, but containing the extracellular region possessing all 5 immunoglobulin-like domains was prepared. A 30 bp mutant oligonucleotide (CTC TCC CCC CGG TTC TAG ATT GTC ATC ATC) was used to transform the codons for amino acids tyrosine (Y) and glutamic acid (E) at positions 452 and 453, respectively, to a phenylalanine (F) and a translational stop codon (TAG). The mutant was isolated by its unique Xba 1 restriction site, and was designated $Y^{452}E/F,TAG$.

To express the mutant protein, COS cells were transfected with three mutuant subclones (#2, #7, and #8). Three days after transfection with the three mutant subclones, culture supernates and cell lysate were analyzed by immunoprecipitation with anti-ICAM-1 monoclonal antibody RR1/1 and SDS-PAGE. ICAM-1 was precipitated from the culture supernates of cells transfected with mutant subclones #2 and #8, but not from detergent lysates of those cells. The molecular weight of ICAM-1 found in the culture supernate was reduced approximately 6 kd relative to the membrane form of ICAM-1, which is consistent with the size predicted from the mutant DNA. Thus, this functional derivative of ICAM-1 is excreted as a soluble protein. In contrast, ICAM-1 was not immunoprecipitated from control culture supernates of cells transfected with native ICAM-1, demonstrating that the membrane form of ICAM-1 is not shed from Cos cells. Furthermore, no ICAM-1 was immunoprecipitated from either culture supernates or cell lysates from negative control mock-transfected cells.

The truncated ICAM-1 secreted from transfected cells was purified by immunoaffinity chromatography with an ICAM-1 specific antibody (R6-5-D6) and tested for functional activity in a cell binding assay. After purification in the presence of the detergent octylglucoside, preparations containing native ICAM-1 or the truncated, secreted form were diluted to a final concentration of 0.25% octylglucoside (a concentration below the critical micelle concentration of the detergent). These preparations of ICAM-1 were allowed to bind to the surfaces of plastic 96-well plates (Nunc), to produce ICAM-1 bound to a solid-phase. After washing out unbound material, approximately 75–80% and 83–88% of SKW-3 cells bearing LFA-1 on their surface bound specifically to the native and to the truncated forms of ICAM-1, respectively. These data demonstrate that the secreted, truncated soluble ICAM-1 functional derivative retained both the immunological reactivity and the ability to mediate ICAM-1 dependent adhesion which are characteristic of native ICAM-1.

A functional derivative of ICAM-1 lacking only the cytoplasmic domain was prepared by similar methods. A 25 bp oligonucleotide (TC AGC ACG TAC CTC TAG AAC CGC CA) was used to alter the codon for amino acid 476 (Y) to a TAG translational stop codon. The mutant was designated $Y^{476}/TAG$. Immunoprecipitation analysis and SOS-PAGE of Cos cells transfected with the mutant detected a membrane bound form of ICAM-1 with a molecular weight approximately 3 kd less than native ICAM-1. Indirect immunofluorescence of the mutant-transfected Cos cells demonstrated a punctate staining pattern similar to naive ICAM-1 expressed on LPS-stimulated human endothelial cells. Finally, cells transfected with the mutant DNA specifically bound to purified LFA-1 on plastic surfaces in a manner similar to Cos cells transfected with native ICAM-1 DNA (Table 2).

TABLE 2

Ability of Cells Expressing ICAM-1 or a Functional Derivative of ICAM-1 to Bind LFA-1

| TRANSFECTION | % of Cells Expressing ICAM-1 that Bind LFA-1 in the Presence of: | |
|---|---|---|
| | No Antibody | RR1/1 |
| Mock | 0 | 0 |
| Native ICAM-1 | 20 | 0 |
| $Y^{476}$/TAG | 20 | 0 |

EXAMPLE 3

Multimeric Forms of ICAM-1 with Increased Biological Half-life Affinity and Clearance Ability Chimeric molecules are constructed in which domains 1 and 2 of ICAM-1 are attached to the hinge region of the immunoglobulin heavy chain. Preferred constructs attach the C-terminus of ICAM-1 domain 2 to a segment of the immunoglobulin heavy chain gene just N-terminal to the hinge region, allowing the segmental flexibility conferred by the hinge region. The ICAM-1 domains 1 and 2 will thus replace the Fab fragment of an antibody. Attachment to heavy chains of the IgG class and production of animal cells will result in the production of a chimeric molecule. Production of molecules containing heavy chains derived from IgA or IgM will result in production of molecules of higher multimericy containing from 2 to 12 ICAM-1 molecules. Co-expression of J-chain gene in the animal cells producing the ICAM-1 heavy chain chimeric molecules will allow proper assembly of IgA and IgM multimers resulting predominantly in IgA molecules containing 4 to 6 ICAM-1 molecules and in the case of IgM containing approximately 10 ICAM-1 molecules. These chimeric molecules may have several advantages. First, Ig molecules are designed to be long lasting in the circulation and this may improve biological half-life.

Furthermore, the multimeric nature of these engineered molecules will allow them to interact with higher avidity with rhinovirus as well as with cell surface LFA-1, depending on the therapeutic context, and thus greatly decrease the amount of recombinant protein which needs to be administered to give an effective dose. IgA and IgM are highly glycosylated molecules normally present in secretions in mucosal sites as in the nose. Their highly hydrophilic nature helps to keep bacteria and viruses to which they bind out in the mucosa, preventing attachment to cells and preventing crossing of the epithelial cell membrane barrier. Thus, they may have increased therapeutic efficacy. IgM and in particularly IgA are stable in mucosal environments and they may increase the stability of the ICAM-1 constructs. If such an ICAM-1 functional derivative is administered in the blood stream, it may also increase biological half-life. IgA does not fix complement and thus would be ideal for applications in which this would be deleterious. If IgG H chain chimerics are desired, it would be possible to mutate regions involved in attachment to complement as well as in interactions with Fc receptors.

A chimeric molecule in which domains 1, 1–2, 1–3, 1–4, or 1–5 of ICAM-1 are joined to the hinge region and CH2 and CH3 domains of IgA is especially suitable for use as a virus inhibitor in the nose. Three IgA H chain sequences have been described (reviewed by Tsuzukida et al., *Proc. Natl. Acad. Sci.* (*U.S.A.*) 76:1104–1108 (1979), which reference is incorporated herein by reference). Standard methods of ligating an ICAM-1 cDNA (cut 3' to the regions indicated above) to an IgA H chain can be used. IgA H chain would be joined at or between residues 221–241 (numbering system of Tsuzukida et al., *Proc. Natl. Acad. Sci.* (*U.S.A.*) 76:1104–1108 (1979)) so that a region of IgA H beginning in this region to the C-terminus of IgA H would be joined to the C-terminal portion of the chimera. ICAM-1 would be analogous to an FAB fragment; no L chain would be needed since VH and CH1 of IgA are not present in the construct.

IgA is specialized to the mucosal environment (Underdown et al., *Ann. Rev. Immunol.* 4:389–417 (1986) and may enhance the stability of ICAM-1 chimeras. In addition, the ability of such molecules to bind to mucopolysaccharides may enhance clearance of rhinovirus or maintenance in the nose.

Furthermore, IgA C regions polymerize. An IgA monomer contains 2 H and L chains; an ICAM-1 IgA H chain chimeric monomer would contain 2 ICAM-1- H chains which would be stabilized by a disulfide in the IgA hinge region as well as non-covalent interactions between CH2 and CH3. These monomer units can be further assembled into dimers and trimers, by a cysteine residue at IgA amino acid position 471, which can link monomers to one another, or to a J chain. Such constructs can be used without co-transfection with J chain constructs to give additional properties and to alter stability. A J chain is not needed to obtain dimeric and trimeric IgA.

Chimerics have the advantage of a multimeric ICAM-1 for multipoint interaction with rhinovirus, raising the affinity and hence lowering the concentration of ICAM-1 needed for neutralization to between $10^{-9}$ M–$10^{-12}$ M. The hinge region of IgA will allow proper orientation for binding to rhinovirus, and is protease resistant due to 0-linked glycosylation. IgA1 and IgA2 and allelic variants of IgA2, A2m (1) and A2m(2) differ in sequence in the hinge and CH domains, and in their susceptibility to proteases (see, Flanagan, J. G. et al., *Cell* 36:681–688 (1984), which reference is incorporated herein by reference).

EXAMPLE 4

ICAM-1 Outline Structure and the LFA-1 and Rhinovirus Binding Sites: Viral Mimicry of a Cell Adhesion Receptor ICAM-1 and a second LFA-1 counter-receptor, ICAM-2, constitute a subfamily of the immunoglobulin (Ig) superfamily (Staunton, D. E., et al., *Cell* 52:925–933 (1988), which reference is incorporated herein by reference). ICAM-1 possesses five Ig-like C domains whereas ICAM-2 possesses two, which are most homologous to the amino terminal domains of ICAM-1. ICAM-1 and ICAM-2, expressed on a variety of cell types, support various leukocyte adhesion dependent functions including induction and effector functions in the immune response. ICAM-1 expression is highly inducible by cytokines and thus the LFA-1/ICAM-1 adhesion system is able to guide leukocyte migration and localization during inflammation (Rothlein, R. *J. Immunol.* 137:1270–1274 (1986); Marlin, S. D. et al., *Cell* 51:813–819 (1987); Kishimoto, T. K. et al., *Adv. Immunol.* 46:149–182 (1989); Dustin, M. L. et al., *Immunol. Today* 9:213–215 (1988), all of which references are incorporated herein by reference).

LFA-1 (CD11a/CD18) is a member of the integrin family most closely related to two other leukocyte integrins Mac-1 (CR3; CD11b/CD18) and p150/95 (CD11c/CD18) (Hynes, R. O., *Cell* 48:549–554 (1987)) Mac-1, in addition to supporting neutrophil adhesion, has been demonstrated to bind several ligands including iC3b, leishmania gp63 and fibrinogen (Ruoslahti, E., et al., *Cell* 44:517–518 (1986); Hynes, R. O., *Cell* 48:549–554 (1987)). Binding to these ligands can be competed with peptides containing either an RGD or KXXDS sequence (Marlin, S. D. et al., *Cell* 51:813–819 (1987)). Neither ICAM possesses an RGD or KXXDS sequence. It is therefore consistent that interaction between ICAM-1 and LFA-1 is not competed with RGD peptides. Thus, the site of contact on ICAM-1 with LFA-1 is not apparent by analogy to many other integrin-ligand interactions.

ICAM-1 has recently been shown to be subverted as a receptor by the major group of rhinoviruses (Greve, J. M. et al., *Cell* 56:839–847 (1989); Staunton, D. E. et al., *Cell* 56:849–853 (1989); Tomassini, J. E. et al., *Proc. Natl. Acad. Sci. (U.S.A.)* 86:4907–4911 (1989), which references are incorporated herein by reference). Rhinoviruses, members of the small, RNA-containing, protein-encapsidated picornavirus family, cause 40–50% of common colds (Rueckert, R. R., In: *Fields Virology*, Fields, B. N. et al. (eds.), Raven Press, NY, (1985) pp 705–738; Sperber, S. J. et al. *Antimicr. Agents Chemo.* 32: 409–419 (1988), which references are incorporated herein by reference). Over 100 immunologically non-crossreactive rhinoviruses have been defined, of which 90% bind to ICAM-1.

X-ray crystallography shows that rhinoviruses are 30 nm in diameter and have icosohedral symetry with 60 copies of each capsid protein (Rossmann, M. G. et al., *Nature* 317:145–153 (1985)) and hence have 60 potential binding sites for ICAM-1. Based on amino acid substitution mutants, and conformational changes induced by the binding of anti-viral drugs, a deep region of depression or canyon in the capsid which runs about its 5-fold axes has been identified (Rossmarn, M. G. et al., *Nature* 317:145–153 (1985); Colonno, R. J. et al., *Proc. Natl. Acad. Sci.* (U.S.A.) 85:5449–5453 (1988); Rossmann, M. G. et al., *Ann. Rev. Biochem.* 58:533–573 (1989)). Residues at the floor of the canyon are implicated in ICAM-1 binding function.

A single ICAM-1 Ig-like domain is predicted to be of approximately the correct dimensions to associate with HRV residues at the canyon floor (Staunton, D. E. et al., *Cell* 56:849–853 (1989)); however, an antibody Fab fragment is predicted to be excluded (Rossmann, M. G. et al., *Nature* 317:145–153 (1985)). Because the antibody combining site of an Fab fragment is too large to come in contact with the canyon floor, receptor specificity may be maintained by relatively conserved residues at the canyon floor while mutations of residues at the canyon rim may allow for new serotypes and evasion of immune surveillance; the "canyon hypothesis" (Rossmann, M. G. et al., *Nature* 317:145–153 (1985); Colonno, R. J. et al., *Proc. Natl. Acad. Sci. (U.S.A.)* 85:5449–5453 (1988); Rossmann, M. G. et al., *Ann. Rev. Biochem.* 58:533–573 (1989)).

The overall size and shape of ICAM-1 is important to understanding how its Ig domains are arranged. Thus far X-ray crystal structures for Ig superfamily members are available only for immunoglobulins and HLA antigens, which have paired Ig domains; however, domains can also be unpaired as evidenced by Thy-1 which contains a single domain.

Three non-cross blocking ICAM-1 MAbs (RR1/1, R6.5, and LB-2) which block binding to LFA-1 also block HRV binding whereas another (CL203) blocks neither LFA-1 nor HRV binding (Makgoba, M. W., et al., In: *Immunobiology of HLA Volume II: Immunogenetics and Histocompatibility*, B. Dupont, ed., New York: Springer-Verlag, pp. 577–580 (1989); Maio, M., *J. Immunol.* 143:181–188 (1989); Staunton, D. E. et al., *Cell* 56:849–853 (1989), which references are incorporated herein by reference). This finding shows that LFA-1 and HRV may bind to an overlapping region on ICAM-1.

Besides ICAM-1, the cell adhesion molecule CD4 and the complement receptor CR2 have recently been found to be subverted as virus receptors by HIV and EBV viruses, respectively (Maddon, P. J., *Cell* 47:333–348 (1986); Fingeroth, J. D., et al., *Proc. Natl. Acad. Sci. USA* 81:4510–4514 (1984), which references are incorporated herein by reference). Further, a molecule with an Ig domain structure similar to ICAM-1 and which may function in cellular adhesion is a polio virus receptor (Mendelsohn, C. L., et al., *Cell* 56:855–865 (1989)). This may be more than coincidental, since cell adhesion and virus adhesion are in principle very similar. It, therefore, appears that the region of the cell adhesion molecule adopted for binding by the virus is similar to the region adapted for binding to the cell adhesion receptor.

Binding sites for LFA-1 and HRV were determined using site-directed mutagenesis. Regions on ICAM-1 were defined by deleting domains and making amino acid substitutions by site-directed mutagenesis. Characterization of the binding site on ICAM-1 for LFA-1 provides insight into the interaction between Ig and integrin superfamily members.

EXAMPLE 5

Generation of ICAM-1 Mutants

Oligonucleotide-directed Mutagenesis

The coding region of an ICAM-1 cDNA in a 1.8 kb Sal1-Kpn1 fragment, was subcloned into the expression vector CDMB (Seed, B. et al., *Proc. Natl. Acad. Sci. (U.S.A.)* 84:3365–3369 (1987)). Based on the method of Kunkel, T., (*Proc. Natl. Acad. Sci. (U.S.A.)* 82:488–492 (1985)) and modifications of Staunton D. et al. (Staunton, D. E. et al., *Cell* 52:925–933 (1988)), this construct (pCD1.8) was used to generate a single strand uracil containing template to be used in oligonucleotide-directed mutagenesis.

Briefly, *E. coli* strain XS127 was transformed with pCD1.8. Single colonies were grown in one ml of Luria Broth (LB) medium (Difco) with 13 μg/ml ampicillin and 8 μg/ml tetracycline until near saturation. 100 μl of the culture was infected with R408 helper phage (Strategene) at a multiplicity of infection (MOI) of 10, and 10 ml of LB medium with ampicillin and tetracycline was added for a 16 hr culture at 37° C. Following centrifugation at 10,000 rpm for one minute, and 0.22 μm filtration of the supernatant, the phage suspension was used to infect *E. coli* BW313/P3 which was then plated on LB agar (Difco) plates supplemented with ampicillin and tetracycline. Colonies were picked, grown in 1 ml LB medium with ampicillin and tetracycline to near saturation and infected with helper phage at MOI of 10. Culture volume was then increased to 250 ml and the cells were cultured overnight. Single strand DNA was isolated by standard phage extraction.

Mutant oligonucleotides were phosphorylated and utilized with the pCD1.8 template in a second strand synthesis reaction (Staunton, D. E. et al., *Cell* 52:925–933 (1988)).

Transfection

COS cells were seeded into 10 cm tissue culture plates such that they would be 50% confluent by 16–24 hrs. COS cells were then washed once with TBS and incubated for 4 hrs with 4 ml RPMI containing 10% Nu sera (Collaborative) 5 μg/ml chloroquine, 3 μg of mutant plasmid and 200 μg/ml DEAE-dextran sulfate. Cells were then washed wit 10% DMSO/PBS followed by PBS and cultured 16 hrs in culture media. Culture media was replaced with fresh media and at 48 hrs post transfection (OS cells were suspended by trypsin/EDTA (Gibco) treatment and divided into 2, 10 cm plates as well as 24 well tissue culture plates for HRV binding. At 72 hrs cells were harvested from 10 cm plates with 5 mM EDTA/HBSS and processed for adhesion to LFA-1 coated plastic and immunofluorescence.

LFA-1 and HRV Binding

LFA-1 was purified from SKW-3 lysates by immunoaffinity chromatography on TS2/4 LFA-1 mAb Sepahrose and eluted at pH 11.5 in the presence of 2 mM $MgCl_2$ and 1% octylgucoside. LFA-1 (10 Ag per 200 μl per 6-cm plate) was bound to bacteriological Petri dishes by diluting octylglucoside to 0.1% in PBS (phosphate buffered saline) with 2 mM $MgCl_2$ and overnight incubation at 4° C. Plates were blocked with 1% BSA (bovine serum albumin) and stored in PBS containing 2 mM $MgCl_2$, 0.2% BSA, 0.025% azide, and 50 μg/ml gentamycin.

$^{51}Cr$-labelled COS cells in PBS containing 5% FCS (fetal calf serum), 2 mM $MgCl_2$, 0.025% azide (buffer) were incubated with or without 5 μg/ml RR1/1 and R6.5 in LFA-1 coated microtiter plates at 25° C. for 1 hour. Non-adherent cells were removed by 3 washed with buffer. Adherent cells were eluted by the addition of EDTA to 10 mM and γ-counted.

For HRV binding studies, COS cells were reseeded in a 24 well plate. One day later, the confluent monolayer was washed twice with 1 ml of RPMI 1640/10 mM $MgCl_2$/25 mM Hepes pH 7.3 (rhinovirus-14 buffer). Transfected COS cells were labeled with 51Cr for binding to LFA-1 coated plastic as previously described (Staunton, D. E., et al., *Nature* 339:61–64 (1989). Immunoprecipitation and indirect immunofluorescence was performed using ICAM-1 MAb RR1/1 (Rothlein, R., et al., *J. Immunol.* 137:1270–1274 (1986)), R6.5 (Rothlein, R., et al., *J. Immunol.* 141:1665–1669 (1988)), LB-1 (Clark, E. A., et al., *Hum. Immunol.* 16:100–113 (1986)) and CL203 (Maio, M., *J. Immunol.* 143:181–188 (1989), all of which references are incorporated herein by reference).

[$^{35}$S]-Met labeled HRV14 (Sherry, B. et al., *J. Virol.* 57:246–257 (1986) which reference is incorporated herein by reference)), 15–25,000 cpm (approximately 107 PFU) in 100 μl of HRV-buffer was added to each well. Binding occurred in 1 hr at 35° C. in a 5% $CO_2$ atmosphere with horizontal rotation (100 rpm). Unbound [$^{35}$S] HRV14 was aspirated, COS cells were gently washed with 150 ml of HRV buffer and then solubilized with 1% SDS in PBS for scintillation counting.

LFA-1 and HRV-14 binding to ICAM-1 mutants was corrected for binding to mock transfected cells and was normalized for the percent of COS cells staining with CL203 mAb and for percent of binding obtained with wild type:

$$\% \text{ binding} = \frac{((\% \text{ mut binding} - \% \text{ mock binding})/\% \text{ mut } CL203 \text{ stain}) \times 100}{(\% \text{ wt binding} - \% \text{ mock binding})/\% \text{ wt } CL203 \text{ staining}}$$

Binding of RR1, R6.5, and LB-2 mAb was normalized to binding of CL203 mAb using Specific Linear Fluorescence Intensity (SLFI):

% CL203=(mAb SLFI)×100)/CL203 mAB SLFI

Percent of wild-type ICAM-1 expressing COS cells that bound to LFA-1 varied from 11–63% (mean=33%); percent of mock-transfected COS cells bindig varied from 0–1%. Percent of [$^{35}$S] methionine-labeled HRV-14 which bound to COS cells expressing wild-type ICAM-1 varied from 6–43% (mean=21%); percent of mock-transfected COS cell binding varied from 0–4%.

[$^{35}$S] HRV14 binding to ICAM-1 coated plastic was performed as described by Staunton, D. E. et al., *Cell* 56:849–853 (1989), which reference is incorporated herein by reference) but with modification of the HRV buffer as indicated. Incubation conditions were 35° C., 5% $CO_2$ for 1 hour with rotation.

Anti-ICAM-1 antibodies such as RR1/1, R6.5, LB-2, or CL203 have been identified. If these antibodies are capable of inhibiting ICAM-1 function, they must be capable of binding to a particular site in the ICAM-1 molecule which is also important to the ICAM-1 function. Thus, by preparing the above-described deletion mutants of ICAM-1, and determining the extent to which the anti-ICAM-1 antibodies can bind to the deletion, it is possible to determine whether the deleted domains are important for function.

EXAMPLE 6

Visualization of ICAM-1 by Electron Microscopy

The ICAM-1 molecule was examined using electron microscopy. In order to visualize the ICAM-1 molecule for electron microscopy, a soluble fragment of ICAM-1 possessing all five extracellular Ig-like domains (FIG. 4) was purified from the culture media of COS cells transfected with an ICAM-1 mutant construct pCDsD1–5.

ICAM-1 was prepared from COS cells in the following manner. COS cells at 50% confluency were transfected by DEAE-dextran method (Kingston, R. E., In *Current Protocols-in Molecular Biology*, Greene Publishing Associates, pp. 9.0.1–9.9.6 (1987)) which reference is incorporated herein by reference) using approximately 0 (mock) or 4 mg of plasmid/10 cm plate.

Secreted ICAM-1 was purified from the supernatants of COS cells transfected with pCDsD1–5 as described by Marlin and Springer (Marlin, S. D. et al., *Cell* 51:813–819 (1987)) with minor modifications as discussed below. Supernatants were harvested between day 4 and 12 post-transfection (200 ng/ml sICAM-1 0.22μ filtered and passed over RR1/1-sepharose (5 ml, 5 mg/ml) at 0.5 ml/min. The column was washed and eluted with 50 mM triethanolamine HCl, 0.15 M NaCl at pH 10 and pH 12.5, respectively, and fractions were neutralized immediately.

Soluble ICAM was dialized into 0.2 M ammonium bicarbonate, 30% glycerol and prepared for electron microscopy by rotary shadowing (Fowler, W. E. et al., *J. Molec. Biol.* 134:241–249 (1979)). Alternatively, the soluble ICAM was sedimented through a 15–40% glycerol gradient, in 0.2 M ammonium bicarbonate, and the ICAM fractions were used directly for rotary shadowing. The sedimentation coefficient was estimated by comparison to standard proteins in another gradient (curve extrapolated from catalase at 11.3 S, and bovine serum albumin at 4.6 S). The 3.5 S estimated for ICAM should be accurate to within ±0.5 S. Length measurements were made from prints magnified to 250,000×, subtracting 1 nm from each end for the estimated thickness of the shell of metal (Fowler, W. E. et al., *J. Molec. Biol.* 134:241–249 (1979)).

ICAM molecules were analyzed by sedimenting them through a glycerol gradient, in 0.2 M ammonium bicarbonate. The ICAM molecules remained near the top of the gradient, at a sedimentation coefficient estimated to be about 3.5 S. For a molecular mass of 92 kD, this indicates a value of $f/f_{min}=2.0$, indicative of a highly elongated molecule (Erickson, H. P., *Biophys. J.* 37:96a (1982)).

Rotary shadowed ICAM molecules appeared as thin rods, which were either straight, or with a single bend. Molecules with a uniform curvature or with two bends were rarely seen, suggesting a rigid rod structure with a single hinge point. Although the angle of the bend was somewhat variable, in most of the obviously bent molecules the angle was close to 90 degrees.

Length measurements gave a value of 16.6±0.24 nm (av.±s.d., n=25) for the straight molecules. For the bent molecules the long arm was 11.8±0.12 nm, and the short arm was 6.9±0.15 nm (n=21). The total length of the bent molecules, 18.7 nm, was somewhat longer than that measured for the straight molecules. It was possible that the population of straight molecules contained some in which the short art was bent toward the viewer, eclipsing the full profile. Thus, the bent molecules provided a more reliable population for length measure-ments. The rod appeared to have a uniform diameter, on the order of 2–3 nm.

The ICAM molecule was found to contain five repeats of IgG-like domains, which have dimension 4×2.5×2 nm. The total length of the ICAM molecule, 18.7 nm, indicates 3.7 nm per IgG repeat, and suggests that the domains are aligned with their long axes at a small angle to the axis of the rod. Models in which two or four of the IgG-like domains are paired with one another are too short. The bend was thus at a point about two-fifths along the rod, suggesting that it occurs between domains 2 and 3 or between domains 3 and 4, and dividing it into a short and a long arm.

EXAMPLE 7

Binding of ICAM-1 Deletion Mutants to LFA-1 and HRV

ICAM-1 is an integral membrane protein, of which the extracellular domain is predicted to be composed of 5 Ig-like C-domains. To localize the site(s) of LFA-1 and HRV contact to a particular ICAM-1 Ig-like domain(s), entire domains were deleted by oligonucleotide directed mutagenesis and tested functionally following expression in COS cells (FIG. 4). In addition, the cytoplasmic domain was deleted to determine its potential contribution to adhesion.

A secreted form of ICAM-1 including domains 1 through 5 was produced by mutation of the two most carboxyl extracellular residues Y452 and E453 to F and a translational stop codon respectively (pCDsD1–5). The entire cytoplasmic domain of ICAM-1 was deleted (DCyt.⁻) by transforming the codon for the carboxyl terminal transmembrane residue Y476 to a translational stop codon. D3 and D4 and 5 were deleted using long (48 bp) mutant oligonucleotides to span distal ICAM-1 sequence such that codons for F185 and P284 (D3⁻) and P284 and R451 (D4⁻5⁻) would be joined (FIG. 4). The desired deletion mutations were confirmed by DNA sequencing.

Following transfection, ICAM-1 mutants possessing deletions of the cytoplasmic (Y476/* or Dcyt.⁻), third (D3⁻) and fourth and fifth (D4⁻5⁻) domains were expressed in 50–60% of COS cells at similar characteristic broad levels (FIG. 5). Immunoprecipitation and SDS-PAGE of Dcyt⁻, D3⁻, and D4⁻5⁻ICAM-1 from COS cells, relative to wild-type, demonstrated a 3, 24 and 23 kD decrease, respectively. Wild-type ICAM-1, approximately 92 kD when expressed in COS cells, has a 55 kD core protein and thus each of the eight linked glycosylation sites may possess an average 4 kD oligosaccharide. Based on the predicted glycosylation of each domain (FIG. 4), the observed decreases in mass are reasonably consistent with the expected decreases of 3, 19 and 27 kD, respectively.

Figure 6:
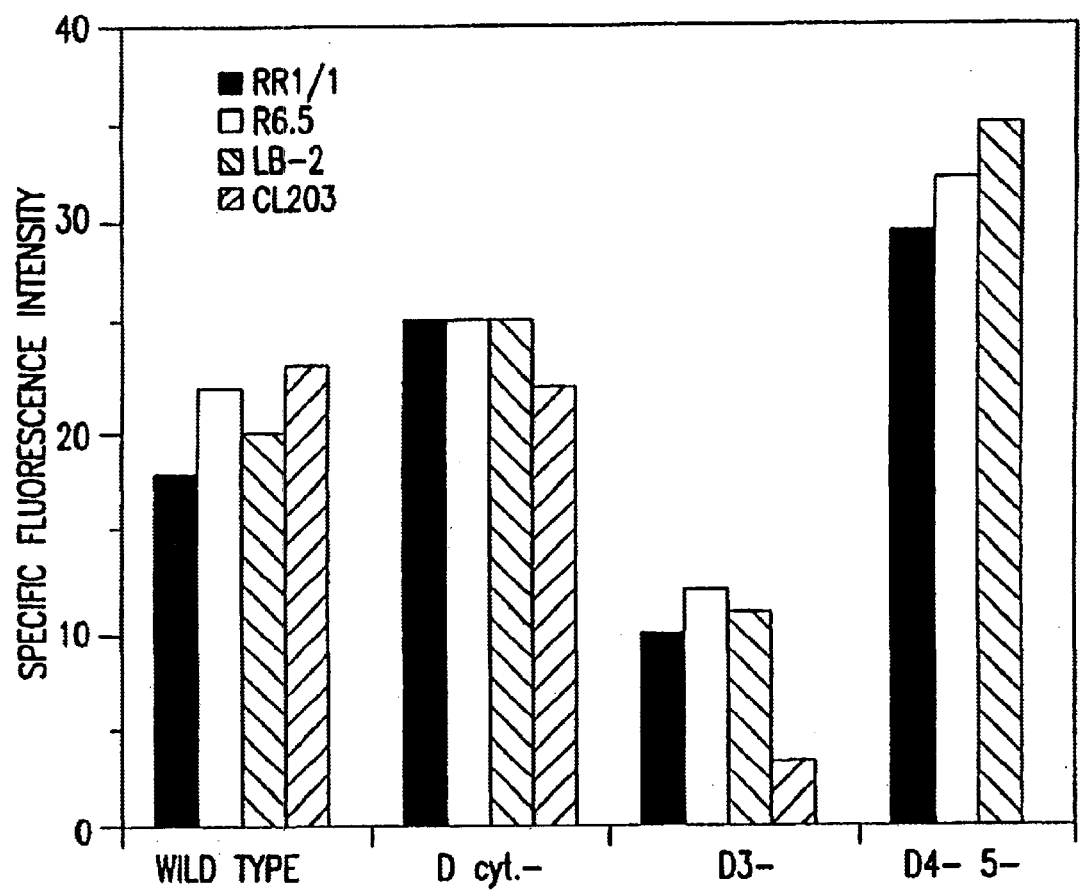
FIG. 6 shows the expression of ICAM-1 deletion mutants in COS cells. COS cells were analyzed by flow cytofluorometry following indirect immunofluorescence with MAbs RR1/1 (solid bar), R6.5 (open bar), LB-2 (stippled bar) or CL203 (hatched bar). Specific fluorescence intensity was determined with background binding to mock transfected cells subtracted.

Efficiency of expression of mutant ICAM-1 in these studies has been examined with a panel of 4 ICAM-1 MAb. These 4 MAb, RR1/1, R6.5, LB-2 and CL203 do not inhibit binding of one another to cell surface ICAM-1 as shown with biotinylated MAb, confirming previous results (Marlin, S. D., et al., *Cell* 51:813–819 (1987), which reference is incorporated herein by reference). They thus bind to four distinct epitopes. Following transfection ICAM-1 deletion mutants were expressed in COS cells at characteristic broad levels (FIG. 5). All MAb bound to the Dcyt mutant at levels equivalent to that of wild type (FIG. 6). Binding of CL203 was decreased upon removal of D3 and eliminated upon removal of D4 and D5. Binding of the other three MAb was unaffected for the D45 mutant and was decreased, although less so than for CL203, for the D3 mutant. Thus the epitopes for RR1/1, R6.5 and LB-2 are located within D1 or 2 and that of CL203 within D4 or 5. The Dcyt and D45 mutants are efficiently expressed while the D3 mutant appears expressed at about one-half the level of wild type.

Figure 7:
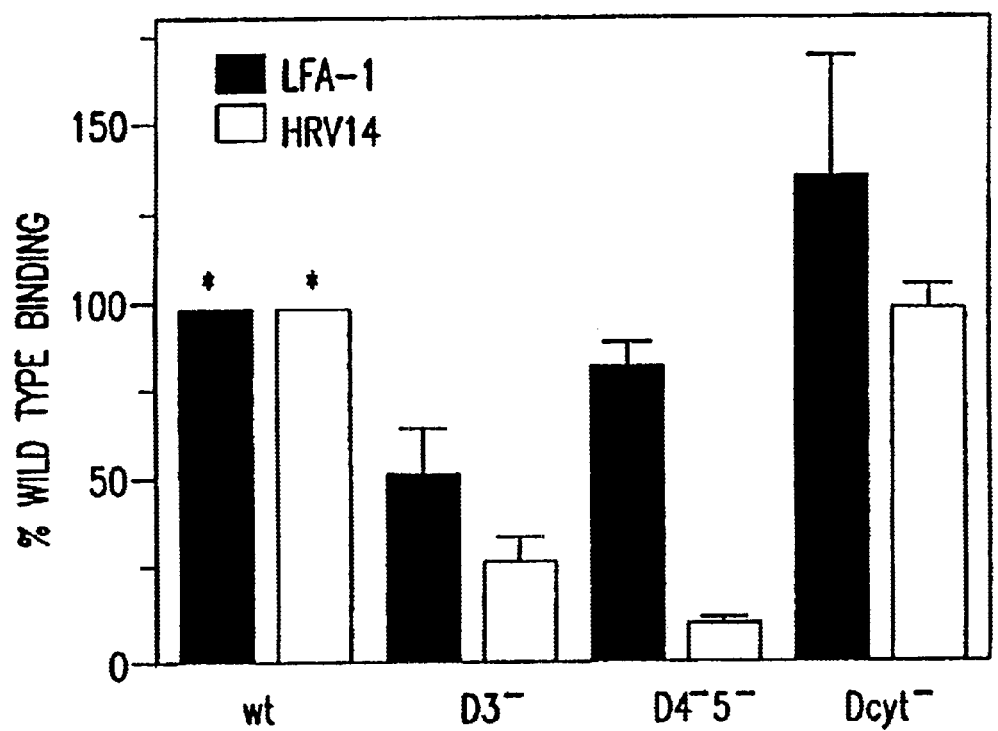
FIG. 7 shows binding of ICAM-1 deletion mutants to LFA-1 and HRV14. COS cells expressing ICAM-1 deletion mutants were tested for adherence to plastic bound LFA-1 and for binding 35S met-labeled HRV14. Standard error for multiple experiments (2–4) are indicated.

COS cells expressing all three deletion mutants adhere specifically to plastic-bound LFA-1 (FIG. 7, closed bars). All 3 deletion mutants demonstrate wild type levels of adherence to LFA-1. Deletion of D4 and 5 had no significant effect on LFA-1 binding while deletion of D3 decreased LFA-1 binding to an extent comparable to its decreased expression. Thus D1 and 2 are sufficient for binding to LFA-1.

Amino acid substitutions in predicted β-turns in domains 1, 2 and 3 were also generated and functionally tested following expression in COS cells. The R6.5 epitope was thus localized to the sequence E111GGA in domain 2 and may also involve E39 in domain 1 whereas RR1/1 and LB-2 are both dependent on R13 in domain 1 (Table 3). In addition, RR1/1 binding is decreased by mutations in the sequence D71GQS. Mutations eliminating N-linked glycosylation sites at N103 and N165 result in decreased RR1/1, R6.5 and LB-2, LFA-1 HRV binding. These mutations appear to effect processing such that ICAM-1 dimers are generated.

Other mutations in domain 2 or 3 did not result in altered LFA-1 adhesion or HRV binding (Table 3). In addition, the residues V4 and E90 may also function in HRV binding.

Thus, LFA-1 and HRV binding appears to be a function of the amino terminal Ig-like domain of ICAM-1. FIG. 3 shows an alignment of ICAM amino terminal domains.

Binding of HRV14 to ICAM-1 domain deletion mutants demonstrates that D1 and 2 is also sufficient for this interaction (FIG. 7, open bars). Domain 3 and the cytoplasmic domain deletion mutants also demonstrate wild type levels of [$^{35}$S]HRV-14 binding whereas, the deletion of domains 4 and 5 results in a decrease in binding to approximately 30% wild type (FIG. 7). The decreased binding to the D3⁻ mutant may be for the same reason mentioned above for LFA-1 binding. However, deletion of D4 and 5 results in a consistent decrease in binding HRV14 which is not found for LFA-1. Thus as the binding site on ICAM-1 becomes immersed into the cellular glycocalyx by the predicted 8 nm shortening when D4 and 5 are deleted, or alternatively as it becomes less flexible, it becomes less accessible to HRV.

The binding of LFA-1 and HRV14 to D1 and 2 and the above-reported mAb epitope localization data correlate with previous mAb blocking data. Thus the ICAM-1 sites which interacts with RR1/1, R6.5 and LB-2 are localized to domains 1 and 2 block both LFA-1 and HRV binding, whereas the ICAM-1 sites which interact with CL203 are localized to domains 4 and 5. CL203 blocks neither cell adhesion nor virus adhesion (Maio, M. et al., *J. Immunol.* 143:181–188 (1989); Staunton, D. E., et al., *Cell* 52:925–933 (1988)), which references are incorporated herein by reference).

EXAMPLE 8

ICAM-1 Amino Acid Substitution Mutants

Features of the hypothetical Ig-like domains of ICAM-1 were used to guide not only the deletion experiments described above but also amino acid substitutions. The three amino-terminal Ig-like domains of ICAM-1 are predicted to possess 7 b strands each. These strands are predicted to be arranged in two sheets, which are connected by the intra-domain disulfide bond to form a "sandwich." The loops connecting the b strands in immunoglobulins form the antigen-binding site, and are hypothesized to be utilized in intermolecular contacts in other Ig superfamily members (Williams, A. F. et al., *Ann. Rev. Immunol.* 6:381–405 (1988), which reference is incorporated herein by reference). The strategy followed was to first introduce two to four amino acid substitutions per loop in domains 1–3. If effects were found, single substitutions were then made. Finally, in some areas of interest substitutions were introduced into b stands.

Mutants of ICAM-1 were generated in the following manner. Oligonucleotide-directed mutagenesis based on the method of Kunkel (Kunkel, T. A., *Proc. Natl. Acad. Sci. USA* 82:488–492 (1985), with modifications by Peterson A. and Seed B. (*Nature* 329:842–846 (1987)), both of which references are incorporated herein by reference) was utilized to generate ICAM-1 deletions and amino acid substitutions. Mutations were made using a single strand uracil-containing template of ICAM-1 cDNA subcloned into the expression vector CDM8 (pCD1.8), which was previously described (Staunton, D. E. et al., *Cell* 56:849–853 (1989)). Mutant ICAM-1 oligonucleotides which confer a unique restriction site were used to prime a second strand synthesis reaction. Following a transformation into *E. coli*, mutants were isolated by screening for the unique restriction sites. In general, two or more isolates of each mutant were tested in binding studies following COS cell transfection.

The results of this experiment are summarized in Table 3. In Table 3, the notation for the mutations uses the one-letter code for the wild-type sequence followed by a slash and the one-letter code for the corresponding mutant sequence. The position of the first amino acid within the sequence is indicated. Wild type residues precede the slash followed by the residues they were substituted for in the mutant. COS cells expressing ICAM-1 mutants were tested for adherence to LFA-1 coated plastic and for binding 35S met-labeled HRV14. LFA-1 and HRV14 binding is normalized for percent of cells expressing mutant ICAM-1 and for binding of wild type expressing cells. Binding is presented as mean and standard error (SE) for multiple experiments (n). Effects of two-fold or greater were reproducible in LFA-1, HRV and mAb binding assays and thus considered significant (bold and underlined). The specific linear fluorescence intensity (SLFI) of CL203 for each mutant is normalized to that of wild type CL203 SLFI (% WT) as discussed above. The SLFI of RR1/1, R6.5 and LB-2 SLFI is normalized to the CL203 SLFI of the mutant (% CL203) as described above.

TABLE 3

Binding of ICAM-1 Amino Acid Substitution Mutants to LFA-1 and HRV14

| Mutation | LFA-1 Binding | | HRV Binding | | CL203 | | SLFI (% CL203) | | |
|---|---|---|---|---|---|---|---|---|---|
| | % | ± SE | % | ± SE | % WT | ± SE | RR/1 | R6.5 | LB-2 |
| D1 | | | | | | | | | |
| Q1T/KA | 119 | 23(2) | 11 | 4(2) | 230 | 61(2) | 94 | 115 | 113 |
| Q1/E | 175 | 53(3) | 149 | 57(3) | 135 | 21(3) | 154 | 145 | 136 |
| Q1/K | 97 | 20(2) | 78 | 29(2) | 168 | 17(3) | 109 | 121 | 106 |
| S3VS/AGL | 18 | 5(3) | 61 | 32(2) | 121 | 21(2) | 5 | 31 | 9 |
| S3/T | 149 | 38(3) | 196 | 72(3) | 224 | 32(3) | 111 | 114 | 117 |
| V4/G | 64 | 17(3) | 30 | 13(4) | 111 | 39(3) | 47 | 73 | 58 |
| S5/T | 104 | 12(2) | 125 | 38(3) | 251 | 24(3) | 107 | 107 | 120 |
| K8/E | 84 | 6(2) | 132 | 18(2) | 111 | 11(2) | 104 | 121 | 110 |
| R13G/EA | 2 | 2(4) | 3 | 1(2) | 132 | 4(2) | 0 | 31 | 0 |
| R13/E | 1 | 1(3) | 10 | 5(3) | 202 | 34(3) | 4 | 48 | 4 |
| R13/K | 98 | 16(3) | 123 | 13(2) | 189 | 45(4) | 133 | 117 | 121 |
| R13/Q | 78 | 23(3) | 60 | 0(2) | 161 | 36(3) | 73 | 73 | 47 |
| G15/SA | 120 | 17(3) | 164 | 23(2) | 172 | 44(2) | 89 | 88 | 89 |
| T20CS/ACT | 91 | 22(3) | 130 | 36(3) | 148 | 24(3) | 86 | 95 | 86 |
| S24/A | 80 | 8(2) | 99 | 7(2) | 158 | 4(2) | 125 | 115 | 125 |
| D26QPK/ALPE | 30 | 13(3) | 13 | 7(3) | 126 | 10(3) | 52 | 89 | 80 |
| Q27/L | 37 | 6(3) | 57 | 26(4) | 33 | 5(4) | 75 | 75 | 125 |
| E34/A | 0 | 0(3) | 66 | 22(4) | 132 | 23(4) | 142 | 150 | 142 |
| K39KE/ERQ | 99 | 25(4) | 61 | 4(3) | 84 | 6(3) | 47 | 93 | 87 |
| K40/A | 124 | 4(2) | 89 | 20(2) | 146 | 4(2) | 123 | 106 | 106 |
| G46NN/ASI | 49 | 15(4) | 9 | 5(2) | 151 | 24(4) | 140 | 107 | 113 |
| N48/H | 88 | — | 81 | 2(2) | 164 | 21(2) | 123 | 94 | 100 |
| R49KV/EKL | 123 | 20(2) | 49 | 22(2) | 233 | 21(2) | 103 | 97 | 52 |
| K50V/EL | 29 | 8(2) | 10 | 8(2) | 103 | 22(2) | 23 | 69 | 23 |

TABLE 3-continued

Binding of ICAM-1 Amino Acid Substitution Mutants to LFA-1 and HRV14

| Mutation | LFA-1 Binding % | ± SE | HRV Binding % | ± SE | CL203 % WT | ± SE | SLFI (% CL203) RR/1 | R6.5 | LB-2 |
|---|---|---|---|---|---|---|---|---|---|
| Y52/F | 72 | 0(2) | 174 | 46(3) | 152 | 10(2) | 90 | 95 | 119 |
| Y52/FA | 138 | 35(2) | 125 | 33(2) | 100 | 0(2) | 141 | 133 | 117 |
| N56V/HM | 121 | 13(2) | 101 | 42(2) | 121 | 21(2) | 106 | 125 | 125 |
| Q58EDS/AKDI | 3 | 3(3) | 0 | 0(2) | 98 | 10(3) | 10 | 22 | 7 |
| Q58/H | 109 | 13(2) | 1 | 1(2) | 135 | 35(2) | 93 | 107 | 93 |
| E59/K | 134 | 50(2) | 105 | 20(2) | 130 | 1(2) | 127 | 109 | 136 |
| E59/Q | 84 | 38(2) | 92 | — | 195 | 25 | 112 | 106 | 125 |
| D60S/KL | 1 | 1(3) | 1 | 0(2) | 105 | 17(2) | 0 | 21 | 0 |
| D60/K | 14 | — | 4 | 0(2) | 89 | 8(2) | 0 | 31 | 0 |
| D60/N | 92 | 33(4) | 89 | 14(3) | 127 | 14(3) | 100 | 138 | 108 |
| D60/Q | 18 | 6(2) | 20 | 8(2) | 80 | 1(2) | 30 | 54 | 31 |
| S61/I | 59 | 18(3) | 111 | 4(2) | 140 | 18(5) | 82 | 100 | 100 |
| Q62PM/API | 104 | 48(3) | 182 | 61(2) | 200 | 29(4) | 59 | 81 | 73 |
| M64/I | 111 | 13(2) | 107 | 3(2) | 183 | 40(2) | 83 | 111 | 116 |
| Y66/T | 135 | — | 204 | — | 144 | — | 109 | 104 | 113 |
| N68/K | 101 | 1(2) | 137 | 23(2) | 153 | 8(2) | 97 | 96 | 102 |
| D71GQS/NGEL | 1 | 1(4) | 21 | 12(3) | 161 | 54(2) | 0 | 48 | 26 |
| D71/E | 118 | 28(2) | 140 | 7(2) | 124 | 6(2) | 89 | 100 | 82 |
| D71/N | 79 | 3(3) | 62 | 1(2) | 109 | 26(4) | 44 | 94 | 83 |
| Q73/H | 12 | 10(4) | 117 | 31(5) | 139 | 27(5) | 21 | 80 | 80 |
| Q73/T | 40 | 12(4) | 133 | 46(2) | 218 | 48(2) | 71 | 86 | 114 |
| S74/A | 70 | 6(2) | 156 | 35(2) | 129 | 29(2) | 119 | 119 | 113 |
| T75/A | 59 | 28(2) | 119 | 8(2) | 153 | 10(2) | 94 | 94 | 115 |
| K77T/ES | 87 | 22(4) | 42 | 14(4) | 151 | 38(3) | 88 | 80 | 84 |
| Y83/S | 42 | 9(2) | 86 | 64(2) | 125 | — | 60 | 70 | 50 |
| E87/K | 65 | 10(5) | 27 | 10(3) | 94 | 12(3) | 64 | 64 | 79 |
| R88V/EA | 95 | 1(2) | 152 | 1(2) | 113 | 14(3) | 74 | 100 | 121 |
| E90/Q | 122 | 45(3) | 157 | 57(2) | 152 | 17(2) | 90 | 92 | 112 |
| E90/K | 34 | 11(2) | 50 | 22(4) | 29 | 5(4) | 100 | 123 | 108 |
| D2 | | | | | | | | | |
| L91/A | 87 | 7(2) | 105 | — | 15 | — | 79 | 142 | 133 |
| G101K/AN | 97 | 55(3) | 140 | 60(2) | 142 | 21(3) | 85 | 85 | 85 |
| N103/K | 12 | 6(2) | 13 | — | 91 | 9(2) | 17 | 60 | 22 |
| E111GGA/KAGS | 103 | 35(3) | 162 | 73(2) | 122 | — | 81 | 0 | 89 |
| N118/Q | 54 | 22(3) | 110 | — | 139 | 9(3) | 93 | 85 | 93 |
| R125/E | 81 | 27(3) | 157 | 15(2) | 145 | 37(2) | 181 | 133 | 104 |
| E127/R | 82 | 29(2) | 131 | 4(2) | 191 | 22(2) | 100 | 119 | 106 |
| K128/R | 109 | 52(3) | 137 | 37(2) | 190 | 35(2) | 100 | 118 | 109 |
| V136GE/GVK | 92 | 53(3) | 117 | 1(2) | 171 | 42(2) | 220 | 172 | 138 |
| R149RD/EEG | 81 | 40(2) | 139 | 56(2) | 159 | 47(2) | 166 | 189 | 166 |
| H152HGA/EEGS | 85 | 52(2) | 82 | 20(2) | 94 | — | 103 | 94 | 112 |
| A115N/SV | 0 | 0(3) | 12 | 8(2) | 60 | 6(2) | 0 | 0 | 0 |
| N156/E | 60 | 4(2) | 107 | — | 182 | 57(2) | 84 | 95 | 95 |
| R166PQ/EPA | 75 | 8(2) | 25 | 8(3) | 94 | 10(3) | 100 | 109 | 64 |
| N175TSA/QTLG | 26 | 10(4) | 40 | 8(3) | 75 | 16(3) | 19 | 50 | 44 |
| N175/A | 67 | 3(3) | 129 | 46(2) | 80 | 9(2) | 162 | 175 | 150 |
| S177/G | 59 | 1(2) | 66 | 6(2) | 87 | 6(3) | 136 | 118 | 90 |
| A178/G | 59 | 3(2) | 102 | — | 304 | — | 63 | 69 | 74 |
| D3 | | | | | | | | | |
| A189T/SI | 91 | 3(2) | 168 | — | 138 | 38(2) | 175 | 166 | 166 |
| D203TQ/TAD | 91 | 53(2) | 111 | 8(2) | 125 | — | 178 | 116 | 86 |
| D213GL/HGV | 90 | 52(3) | 99 | 13(2) | 128 | 28(2) | 231 | 175 | 107 |
| D229QR/HLE | 90 | 37(3) | 106 | 11(2) | 210 | 59(2) | 94 | 92 | 100 |
| N240DS/KNA | 147 | 29(3) | 82 | 32(2) | 142 | — | 113 | 125 | 132 |
| E254DE/KEK | 122 | 33(3) | 99 | 23(2) | 180 | 63(2) | 178 | 129 | 81 |
| N269QSQI/IQAEQ | 101 | 9(2) | 108 | 45(2) | 95 | 15(3) | 162 | 150 | 150 |

Since the epitope of mAb CL203 localizes to D4 or 5, whereas D1–D3 were subjected to amino acid substitutions, CL203 was used to determine the level of expression of ICAM-1 amino acid substitution mutants in transfected COS cells. Binding of ICAM-1 mutants to LFA-1 and HRV was normalized with respect to mAb CL203 binding and to binding obtained with wild-type ICAM-1. Furthermore, since mAb RR1/1, R6.5, and LB-2 bind to distinct epitopes, a loss of two or more of these epitopes indicates a gross disruption of structure and thus corresponding effects on LFA-1 and HRV binding were discounted. Two mutations, Q27/L and E90/K, which demonstrate a specifically reduced level of expression as measured with CL203, were also discounted as lower expression may reflect decreased efficiency of folding of D1 where these mutations occur.

Amino acid substitution mutants which demonstrate a decrease in the binding of only one ICAM-1 mAb suggests that the corresponding wild-type residues contribute to the mAb epitope (Table 3). Decreased binding of mAb to amino acid substitution mutants demonstrates that the epitope for RR1/1 involve the residues D71 and Q73 and sequences at 026, K39 and Q62. The epitope for R6.5 is completely and specifically disrupted by a mutation in the sequence at E111 in D2. LB-2 binding is specifically affected by mutations in sequence at R49 in D1 and R166 in D2.

Domains 1 and 2 appear to be conformationally linked. Twelve of 53 mutations in D1, and a similar proportion in D2, 4 of 18, disrupt binding of RR1/1, R 6.5, and LB.2 mAb, LFA-1, and HRV. Since these ligands bind to different sites (the mAb) or only partially overlapping regions (LFA-1 and HRV, see below), the ability of mutations widely spread throughout both D1 and D2 to have common effects suggests that the conformation of D1 is dependent on the conformation of D2 and vice versa. In contrast, none of the mutations in D3 affect binding of these ligands, and none of these mutations affects binding of CL203 which localizes to D4 or D5. This indicates that there is substantial contact between D1 and D2, but that D1 and D2 are conformationally independent of D3; i.e., there may be a hinge between D2 and D3. The most disruptive mutations involve residues R13 and D60 which would be predicted in an Ig-model (see below) to come into close proximity to residues in D2. Deletion of residues in D2 (residues P95-A189) has resulted in a lack of cell surface expression, further indicating that proper folding of ICAM-1 depends on D1 and D2 interactions.

Conformational disruption in two mutations is reflected in abberent disulfide bond formation. Immunoprecipitation and non-reducing SDS-PAGE of 12 D1 and D2 mutants revealed that two of them, N103/K and A155N/SV, to be ICAM-1 disulfide linked dimers. Residues N103 and N156 occur close to C108 and C159 which are predicted to form the intra-domain disulfide bridge of D2.

Mutations with the strongest effect on LFA-1 binding localized to D1. The most dramatic mutations are E34/A which completely eliminates LFA-1 binding and Q73/H, which decreases it 10-fold (Table 3). A different substitution at Q73, Q73/T, demonstrated a two-fold decrease. The mutations D26QPK/ALPE and G46NN/ASI decrease LFA-1 binding 2-3 fold. In the second domain the mutants N118/Q, N156/E, N175/A and S177/G specifically decreased LFA-1 binding approximately two-fold. These four mutants were found to affect three of the four N-linked glycosylation sites in D2; there are no N-linked glycosylation sites in D1 (FIG. 4). Thus, N-linked carbohydrate may have a small but not critical role in LFA-1 binding. The effect of these mutations may be more indirect. One indirect effect D2 N-linked glycosylation may have is a change in the flexibility of the hinge. None of the mutations in D3 affected LFA-1 binding, in agreement with the lack of effect of deleting D3.

A number of mutations demonstrate that D1 is more important than D2 in HRV binding and that HRV and LFA-1 binding sites partially overlap. Seven mutants decrease HRV14 binding but have no effect on LFA-1 binding. The two which demonstrated the greatest effect involved amino acid substitutions in D1. Q58/H virtually eliminated HRV14 binding and Q1T/KA resulted in a ten-fold decrease. Four other mutations in D1 demonstrated a specific two-fold effect on HRV binding, K39KE/ERQ, R49KV/EKL, D71/N and K77T/ES. One mutation in D2, R155PQ/EPA, resulted in a four-fold decrease in HRV14 binding. D3 mutations did not affect HRV binding.

Of the 4 D1 mutations discussed above which affect LFA-1 binding, 3 affect HRV binding as well. The mutants, D26QPK/ALPE and G46NN/ASI, affected HRV14 binding ten-fold and LFA-1 binding two- to three-fold. The E34/A that totally eliminates LFA-1 binding decreases HRV binding 2-fold. Four mutations in D2 that decreased LFA-1 binding had little or no effect on HRV binding.

Thus residues which were identified as critical (ten-fold or greater affect) to LFA-1 or HRV binding demonstrated a separation in function. The mutations E34/A and Q73/H which markedly decrease LFA-1 binding have a weak or a non-detectable affect on HRV binding. Conversely, mutations have been described above that have a profound affect on HRV binding yet do not affect LFA-1 binding. An overlap in binding sites is, however, demonstrated by two mutations which affect both LFA-1 and HRV binding. In addition, proximity of binding sites is suggested by mutations which are adjacent in sequence position yet affect binding of either LFA-1 or HRV (discussed further below).

Ten sequences/residues important to LFA-1 and HRV14 binding were defined in D1 in contrast to one sequence and potentially three N-linked glycosylations in D2. Residues or sequences critical to binding were identified in D1, not in D2. Further, none of the substitutions in D3 altered binding to LFA-1 or HRV14 confirming the results of deleting D3. Thus the primary site of LFA-1 and HRV14 contact is located in D1.

Figure 8:
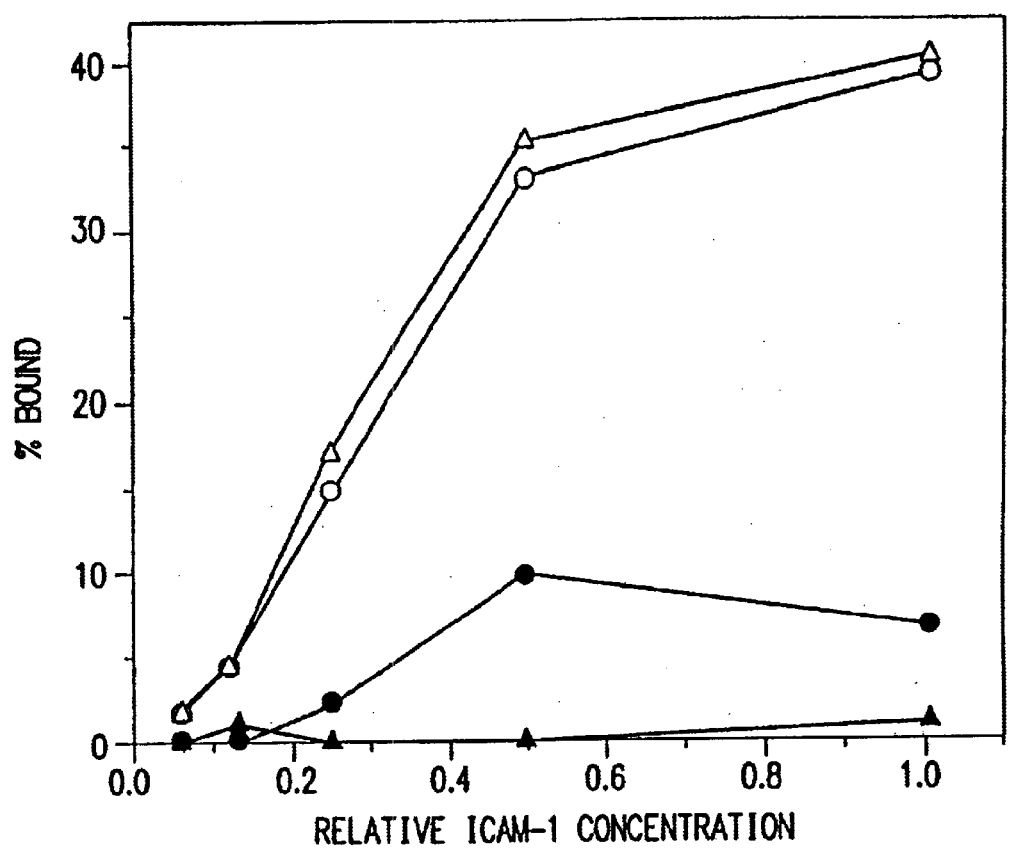
FIG. 8 shows binding of HRV14 to ICAM-1 in the absence of divalent cations. Binding of 35SHRV14 to increasing concentrations of plastic bound ICAM-1 occurred in HRV-buffer with 10 mM Mg++ (open circles) or HRV-buffer minus added Mg++ but with 5 mMEDTA (open triangles). SKW3 binding was in HRV buffer with 0.5 mMMg++ (solid circles) or 5 mM EDTA (solid triangles).

The interaction of LFA-1 and HRV14 was further compared with regard to the requirement for divalent cations. It had previously been demonstrated that ICAM-1 on the cell surface or bound to plastic binds cell surface or purified LFA-1 in a $Mg^{2+}$ dependent manner (Marlin, S. D., et al., Cell 51:813–819 (1987); Staunton, D. E., et al., Nature 339:61–64 (1989)). The binding of the LFA-1 expressing T lymphoma line SKW3 and HRV to purified ICAM-1 was compared on a plastic substrate. Purified ICAM-1 bound to plastic was utilized and the LFA-1 expressing T-cell line was found to bind ICAM-1 only in the presence of $Mg^{2+}$ (FIG. 8). In contrast, the binding of HRV14 to ICAM-1 did not significantly differ in the presence of 10 mM $Mg^{2+}$ or 5 mM EDTA. This was confirmed over a range of ICAM-1 densities on the substrate. The LFA-1:ICAM-1 and HRV:ICAM-1 interaction are thus distinctly different in divalent cation requirements.

The above experiments demonstrate that the extracellular region of ICAM-1 exists as a 20 nm hinged rod. This indicates that the five predicted Ig-like domains are extended and unpaired, and are alligned end-to-end rather than side-by-side. ICAM-1 is thus similar in overall structure to NCAM (Beckers, A., et al., Immunochem. 11:605–609 (1974)). The total length of extracellular ICAM-1 is 18.7 nm and therefore 3.7 nm per Ig domain. The long arm of NCAM, which comprises five IgG-like domains, had a length of 17.6–18.7 nm, essentially identical to the total length of the ICAM molecule (Beckers, A., et al., Immunochem. 11:605–609 (1974)).

Another striking similarity in the structure of ICAM and NCAM is that both molecules have a bend, typically at 90 degrees but with variation indicating flexibility. In ICAM this bend is probably between two IgG-like domains, giving a long arm with three domains and a short arm with two. The finding that the conformation of D1 and D2 are dependent upon one another indicates that the hinge is located between D2 and D3. The sequence at the D2–D3 border demonstrates the most proline rich region in ICAM-1 (4 prolines within 10 residues). This is consistent with Ig hinge sequences which are characteristically proline rich. Indeed, all 4 prolines in this region are spaced identically to 4 prolines in the hinge region of mouse IgG3.

In NCAM there is no bend within the five IgG-like domains (these form the apparently rigid long arm equal to the total length of ICAM); rather, the bend immediately follows the sequence of IgG-like domains. The short arm of NCAM contains two fibronectin-like domains, the membrane spanning segment and cytoplasmic domain (Beckers, A., et al., *Immunochem.* 11:605–609 (1974)).

Remarkably, the cell adhesion molecule LCAM, which has no IgG-like domains and is unrelated to ICAM or NCAM, also has a 90 degree bend (Becker, J. W., et al., *Proc. Natl. Acad. Sci. (U.S.A.)* 86:1088–1092 (1989)).

This common feature of cell adhesion molecules would thus appear to be functionally important to permit an extended segment of the molecule, rather than just the tip, to face and form an interface with its receptor. It would allow binding sites located on the distal, flexible segment to bind to receptors oriented at different angles and located at varying distances with respect tot the membrane of the cell bearing the ICAM-1 molecule. Furthermore, segmental flexibility provided by the hinge should increase the rate of diffusion of the binding site within the volume of solvent above the cell surface to which it is limited by its membrane tether, thereby enhancing the kinetics of binding to adhesion receptors or viruses and increasing the efficiency of these interactions.

The rod-shaped unpaired domain organization of ICAM-1 thus facilitates adhesion by elevating binding sites to a critical distance above the cell surface. Rhinovirus binding was more-sensitive than LFA-1 binding to deleting domains 4 and 5, which is predicted to shorten ICAM-1 by 7.4 nm and affect its-flexibility. This may be related to 2 differences between rhinovirus and LFA-1. First, the binding site on HRV is proposed to be submerged in a 2.5 nm deep cleft within a canyon which forms a moat around the five-fold axis of the virion (Rossmann, M. G., et al., *Nature* 317:145–153 (1985)), while electron microscopic studies of integrins suggest a 10×8 nm globular binding domain supported on 18 nm-long stalks above the cell surface (Carrell, N. A. et al., *J. Biol. Chem.* 260:1743–1749 (1985); Nermut, M. V. *EMBO J.* 7:4093–4099 (1988)). The cellular glycoclyx (Williams, A. F. et al., *Ann. Rev. Immunol.* 6:381–405 (1988)) into which ICAM-1 is submerged by its shortening may repel the bulkier rhinovirus more than LFA-1. Second, binding of multiple ICAM-1 molecules to rhinovirus (Colonno, R. J. et al., *Proc. Natl. Acad. Sci. (U.S.A.)* 85:5449–5453 (1988)) would require close proximity of the ICAM-1 molecules one to another, and this packing may be hindered by shortening or loss in flexibility. LFA-1 interaction with ICAM-1 also requires multivalent interactions, but the LFA-1 molecules may well be separated from one another, and, based on content of one alpha and beta subunit each, are predicted to have one binding site each.

Figure 9:
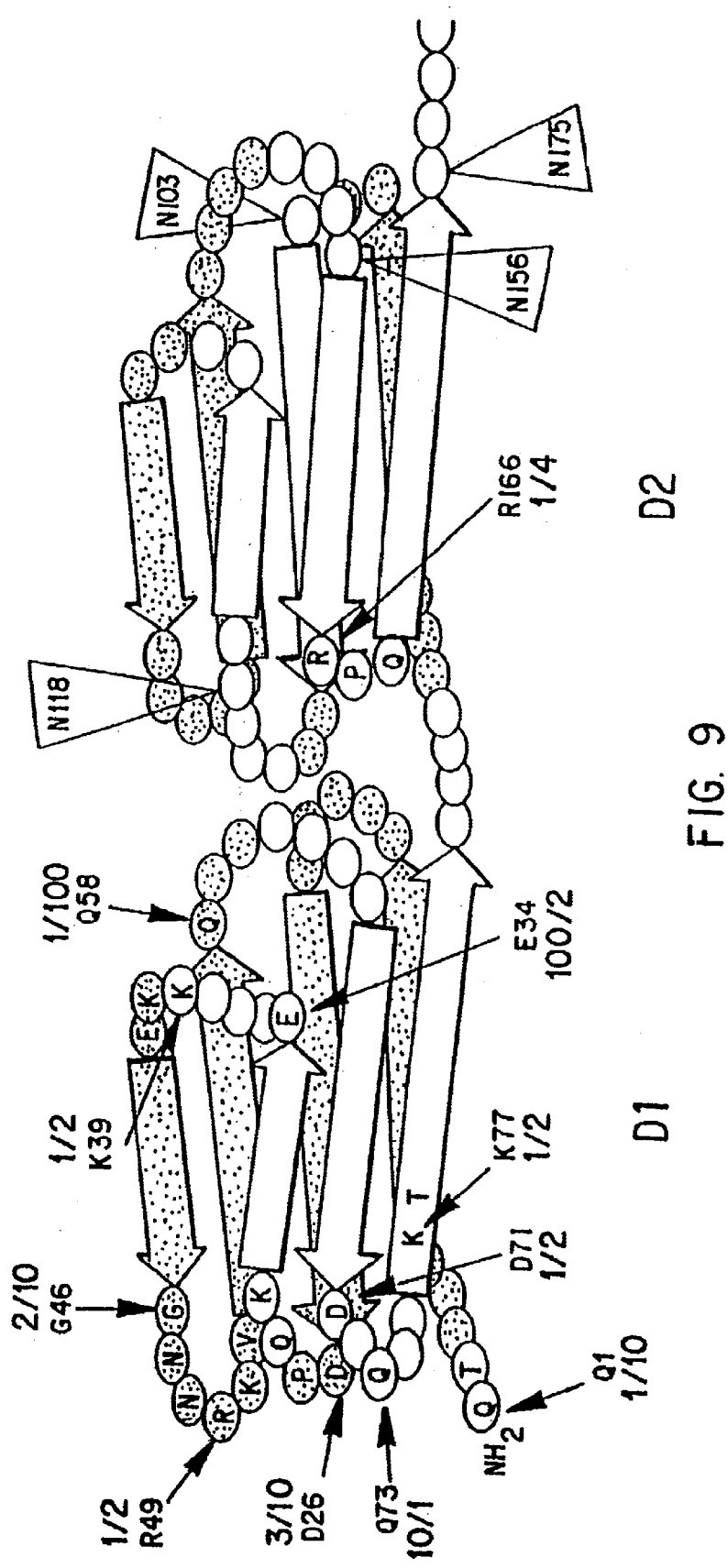
FIG. 9 shows a model of ICAM-1 D1 and D2 tertiary structure: Localization of LFA-1 and HRV binding sites. The basic tertiary structure of an Ig constant domain (Wright, S. D., et al., *Proc. Natl. Acad. Sci. USA* 85:7734–7738 (1988)) was modified to accommodate the predicted b strands (wide arrows) and b turns of ICAM-1 D1 and D2 (Staunton, D. E., et al., *Nature* 339:61–64 (1989a)). Residues involved in LFA-1 or HRV14 binding are indicated. The effect of their corresponding mutations on LFA-1/HRV14 binding (X-fold decrease) is indicated, respectively (outline print). The position of D2 N-linked oligosaccharides (open triangle) are indicated.

The unpaired domain nature of ICAM-1 and the location of sequences/residues involved in binding to D1 is consistent with ICAM-1 D1 binding within the deep cleft of the proposed HRV canyon binding site. The interface of ICAM-1 and HRV may be envisioned in at least two different models. Based upon predicted secondary structure, ICAM-1 sequences were positioned in an Ig fold model (FIG. 9). Four of the six D1 sequences which were implicated in HRV contact Q1T, D26QP, G46NN, and R49KV, locate in this model to the distal half of D1. The dimension of the deep cleft (3–1.2 nm wide and 2.5 nm deep) is such that slightly more than half an Ig-like domain (4 nm long and 2.5–2 nm wide) could be inserted. The distal half of ICAM-1 D1 may therefore bind to residues within the cleft such that the long axis of D1 is approximately perpendicular to the surrounding surface of the virion. The distance between the boundary of each deep cleft, approximately 4 nm, is great enough to allow an ICAM-1 to occupy all five clefts around the five-fold axis of the virion. Other sequences implicated in HRV contact, K39KE, Q58 and R166PQ may interact with HRV residues in the rim of the canyon. Alternatively, these residues in D1 and 2 may not form bonds with HRV residues but contribute inter or intra domain bonds important to binding conformation. A second model of ICAM-1: HRV interaction would be ICAM-1 D1 contacting residues of the cleft such that the long axis of D1 would form an acute angle with the surrounding virion surface. Thus D1 would be more parallel and horizontal with the canyon. This may result in blocking by steric hindrance of some sites around the five-fold axis.

Because 3 non-crossblocking ICAM-1 mAb block both LFA-1 and rhinovirus-14 binding it was suggested previously that LFA-1 and rhinovirus-14 contact sites on ICAM-1 are in close proximity (Staunton, D. E. et al., *Cell* 56:849–853 (1989)). Our present studies show the binding site for rhinovirus-14. We have modeled these sequence positions on ICAM-1 domains 1 and 2 (FIG. 9) assuming an Ig domain structure (Williams, A. F. et al., *Ann. Rev. Immunol.* 6:381–405 (1988)) although the Ig fold may differ in some important way for Ig family members with unpaired domains. Characterization of the mutants G46NN/ASI, D26QPK/ALPE and E34/A reveals common use of ICAM-1 sequences in LFA-1 and rhinovirus-14 binding. The predicted location of contact sequences in the Ig domain model is consistent with close proximity or overlap of LFA-1 and rhinovirus-14 binding sites. Residues implicated in LFA-1 binding, such as Q73 and G46, are proximal to residues implicated in rhinovirus-14 binding, D71 and R49. Thus rhinovirus-14 appears to have evolved to bind to a site on ICAM-1 which overlaps with the LFA-1 binding site. The two binding sites are clearly distinguished, however, by mutations at E34 and Q58 which dramatically and selectively abolish LFA-1 and rhinovirus binding, respectively. Three of the four D1 sequences implicated in LFA-1 contact and 6 of the 9 sequences implicated in rhinovirus-14 contact locate to the membranedistal half of D1 in this model; however, some of the sites where mutations. have the most dramatic effect localize to the proximal half. The overlap of rhinovirus and LFA-1 binding sites in domain 1 appears to be a consequence of the favorability of this domain as an adhesive interaction site as outlines above. Alternatively, ICAM-1 might be a receptor with a triggering function in antigen-presenting cells. In this scenario, binding to domain 1 would trigger through ICAM-1 a response that would be advantageous to rhinovirus, for example by stimulating nasal secretions that would help spread the virus to other people. This would be an example of evolutionary mimicry.

The contact site on ICAM-1 differs from that of many other integrin ligands in sequence and structure. Many integrins which bind extracellular matrix proteins bind to an RGD or an RGD-like sequence in their ligands (Ruoslahti, E., et al., *Cell* 44:517–518 (1986); Hynes, R. O., *Cell* 48:549–554 (1987)). Human ICAM-1 has no RGD sequences but several RGD-like sequences (Simmons, D. et al., *Nature* 331:624–627 (1988); Staunton, D. E. et al. *Cell* 52:925–933 (1988)); murine ICAM-1 contains an RGD sequence. However, none of these sites correspond to residues defined by our mutagenesis studies as important in LFA-1 binding to ICAM-1. Instead of a contiguous sequence like RGD, a number of discontiguous sequences in ICAM-1 appear to be recognized. This is similar to Ig binding to protein antigens in which residues in three noncontiguous complementary-determining regions confer recognition specificity (Alzari, P. M. et al., *Ann. Rev. Immunol.* 6:555–580 (1988)).

ICAM-1 is able to bind another leukocyte integrin, MAC-1, which also binds ligands such as iC3b and fibrinogen in an RGD dependent manner. The site on ICAM-1 which binds MAC-1, however, appears to differ from that which binds LFA-1. Thus MAC-1 binds to an RGD-like sequence on ICAM-1 which would be more consistent with its other binding specificities.

ICAM-1 residues which have been defined above as being important to LFA-1 binding are conserved in other ICAMs. Human ICAM-1 is 50% identical to murine ICAM-1 and 35% identical to human ICAM-2 (Staunton, D. E., et al. *Nature* 339:61–64 (1989)). The residues that are most critical to LFA-1 binding, E34 and Q73, are conserved both in mouse ICAM-1 and in human ICAM-2. This is consistent with the ability of both mouse ICAM-1 and human ICAM-2 (Staunton, D. E., et al. *Nature* 339:61–64 (1989)) to bind to human LFA-1. One D2 N-linked glycosylation site at N156, which influences LFA-1 binding, is also conserved in ICAM-2. Several residues that are important to rhinovirus-14 binding, Q58, G46, D71, K77 and R166, are not conserved in mouse ICAM-1 or human ICAM-2 which is consistent with the apparent inability of mouse cells (Colonno, R. J. et al., *J. Virol.* 57:7–12 (1986)) and ICAM-2 to bind rhinovirus-14.

Sequences important to LFA-1 and HRV contact also correspond to blocking mAb epitopes of RR1/1 and LB-2 whereas the R6.5 epitope does not appear to, and thus may block, binding by steric hindrance.

Binding of LFA-1 to ICAM-1 is dependent on divalent cations. All integrin α subunits have 3 or 4 tandem repeats of "EF hand"-like divalent cation binding sites (Kishimoto, T. K. et al., *Adv. Immunol.* 46:149–182 (1989)). However, these sites differ from the classical EF-hand motif in that they lack one conserved glutamic acid which coordinates with divalent cations (Corbi, A. L. et al., *EMBO J.* 6:4023–4028 (1987)). It has been hypothesized that this residue missing from the integrin may be replaced by a residue in the ligand, and thus that the metal may coordinate with both the receptor and the ligand (Corbi, A. L. et al., *EMBO J.* 6:4023–4028 (1987)). The ICAM-1 residue most critical to binding LFA-1, glutamic acid 34 (E34), might provide the hypothesized coordination with the divalent cation. A similar mechanism does not appear to be present in rhinovirus-14 binding to ICAM-1, which has been found to be divalent cation independent. Previous suggestions of a divalent cation requirement for rhinovirus binding (Rueckert, R. R., In: *Fields Virology*, Fields, B. N. et al. (eds.), Raven Press, NY, (1985) pp 705–738) appear to be based on work with minor group serotypes, which bind to a distinct receptor. Stability as opposed to binding may be influenced by cations that coordinate asparagine 141 at the 5-fold axis of rhinovirus (Rossmann, M. G., et al., *Nature* 317:145–153 (1985)).

ICAM-1 and CD4 are members of the Ig superfamily which demonstrate striking parallels in their function in both cellular and viral adhesion. CD4 is an adhesion receptor on T cells that binds to MHC class II molecules, and is also utilized as a receptor by HIV virus. CD4 has 4 extracellular domains. Recent studies on CD4 have found that mutations in the amino-terminal Ig-like domain have the strongest effect on binding of MHC class II and HIV, with a lesser effect of mutations in the second domain. The binding sites for MHC class II and HIV are overlapping but distinct (Peterson, A. et al., *Cell* 54:65–72 (1988)); Clayton, L. K. et al., *Nature* 339:548–551 (1989); Lamarre, D. et al. *Science* 245:743–746 (1989); Landau, N. R. et al., *Nature* 334:159–167 (1988), all of which references are incorporated herein by reference). Some CD4 mAb epitopes appear to involve residues from both D1 and 2 demonstrating close physical association of these domains (Landau, N. R. et al., *Nature* 334:159–167 (1988)). In all these respects, findings on the cell adhesion and virus binding sites of ICAM-1 and CD4 are similar.

At least two different models may be envisioned for binding of ICAM-1 domain 1 to the putative receptor site in the rhinovirus canyon. As mentioned above, the majority (6 out of 9) of D1 sequences implicated in rhinovirus-14 contact may locate to the distal half of D1 (FIG. 9). The receptor binding site in the rhinovirus canyon has been implicated to be in a deep cleft, 3 nm wide at the top, 1.2 nm wide at the bottom, and 2.5 nm deep (Rossmann, M. G., et al., *Nature* 317:145–153 (1985); Colonno, R. J. et al., *Proc. Natl. Acad. Sci.* (U.S.A.) 85:5449–5453 (1988); Rossmann, M. G. et al., *Ann. Rev. Biochem.* 58:533–573 (1989)). The dimensions of this cleft are such that slightly more than half of an Ig-like domain (4 nm long and 2–2.5 nm wide) could be inserted. Thus the contact sequences in the distal half of ICAM-1 D1 may form bonds with residues within the cleft such that the long axis of D1 is approximately perpendicular to the floor of the canyon. The distance between the center of each deep cleft around the 5-fold axis, approximately 5 nm, is great enough to allow an ICAM-1 molecule to occupy all 5 clefts. The remaining sequences implicated in rhinovirus-14 contact, K39DE, Q58 and R166PQ, that may not locate to the distal half of D1 might interact with rhinovirus-14 residues in the rim of the canyon.

A second model of ICAM-1/rhinovirus-14 interaction would be that ICAM-1 D1 contacts residues of the cleft such that the long axis of D1 would form a more acute angle with the floor of the canyon, allowing D1 and D2 to lie more lengthwise in the canyon. This may result in blocking by steric hindrance of some neighboring rhinovirus-14 binding sites.

Thus, the present invention resolves major points of contact between ICAM-1 and LFA-1 or HRV. Identification of ICAM-1 contact sequences provides additional information for the design of ICAM-1 fragments and synthetic peptides which inhibit LFA-1 and/or HRV binding. For example, the data shows that an ICAM-1 fragment consisting of D1 alone will be sufficient to inhibit both LFA-1 and HRV interaction; however, results presented here suggest that an even more efficient binding conformation will contain both D1 and D2. Since discontinuous ICAM-1 sequences appear to be involved in contact, a long peptide fragment or several shorter peptides which span multiple contact sequences may be used to compete LFA-1 and HRV interactions.

Thus, the identification here of the important binding sites within the first 2 domains of ICAM-1 demonstrates that soluble fragments of ICAM-1 possess potential therapeutic utility in preventing rhinovirus infection and in the treatment of inflammatory disorders and conditions (such as reperfusion injury, transplantation, etc.). Such agents may be effective in therapeutic treatment of 50% of cases with common cold symptoms which are caused by the major group of rhinoviruses (Sperber, S. J. et al. *Antimicr. Agents Chemo.* 32: 409–419 (1988)). In reperfusion injury, leukocytes migrate into and damage tissues temporarily deprived of blood flow. Significant damage due to reperfusion injury in myocardial infarct and ischemic shock has been shown to be blocked by mAb to LFA-1 and other leukocyte integrins (Vedder, N. B. et al., *J. Clin. Invest.* 81:939–944 (1988); Simpson, P. J. et al., *J. Clin. Invest.* 81:624–629 (1988); which references are incorporated herein by reference).

Thus, in summary, LFA-1 (CD11a/CD18) on lymphocytes binds to ICAM-1 (CD54) on other cells to promote critical cell-cell adhesion during immune and inflammatory responses; furthermore, the major group of human rhinoviruses (HRV) utilized ICAM-1 as its cellular receptor. Electron micrographs show the ICAM molecule to be a rod, about 19 nm long. The rod frequently has a 90 degree bend, giving a 12 nm long arm and a 7 nm short arm. These dimensions suggest a model in which the 5 Ig-like domains are oriented at a small angle to the rod axis, with three domains in the long arm and two in the short arm. ICAM-1 sequences important to binding LFA-1, HRV, and 4 monoclonal antibodies (mAb) were identified through the characterization of ICAM-1 mutants possessing deletions of its Ig-like domains and amino acid substitutions in predicted b turns. The amino-terminal 2 Ig-like domains (D1 and D2) of ICAM-1 appear to conformationally interact, and N-linked glycosylation sites in D2 appear to be important to the structural integrity and may have a minor effect in LFA-1 binding. The amino-terminal Ig-like domain of ICAM-1 (D1) contains the primary site of contact for both LFA-1 and HRV. The binding sites appear overlapping but distinct; HRV binding also differs from LFA-1 in the lack of divalent cation dependence. Although LFA-1 is an integrin, it does not recognize a RGD or RGD-like sequence in ICAM-1. Overall, the analysis suggests that rhinoviruses mimic LFA-1 in the choice of binding site ICAM-1, raising the possibility that this is an evolutionary adaptive site.

EXAMPLE 9

A Soluble Functional Derivative of ICAM-1 Inhibits Rhinovirus Infection

As discussed above, rhinoviruses belong to the picornavirus family and are responsible for many common colds (Sperber, S. J. et al., *Antimicrob. Agents Chemother.* 32:409–419 (1988)). The majority of rhinoviruses and some coxsackie viruses (also picornaviruses) share a common cell surface receptor on human cells. ICAM-1 is the cellular receptor for the major subgroup of rhinoviruses (Staunton, D. E. et al., *Cell* 56:849–853 (1989); Greve, J. M. et al., 56:839–847 (1989)), and anti-ICAM-1 antibodies are capable of blocking the binding of major group rhinovirus to cells. In view of this finding, the ability of soluble ICAM-1 functional derivatives to block the binding of major group rhinovirus to cells was investigated.

As discussed above, in order to produce a truncated, soluble derivative of ICAM-1, lacking the cytoplasmic domain, an in-frame stop codon (between the Dcyt and D5) was generated using oligonucleotide-directed mutagenesis based on the method of Kunkel (Kunkel, T. A., *Proc. Natl. Acad. Sci. USA* 82:488–492 (1985)) as modified by Peterson and Seed (Peterson, A. et al., *Cell* 53:65–72 (1988)). This experiment resulted in the formation of a mutant ICAM-1 gene, designated Y452 E/F TAG, which, upon expression resulted in the production of a truncated, secreted form of ICAM-1 (sICAM-1) by the mutant (see Example 8).

An expression vector consisting of the hamster DHFR gene and the coding region of the above-described mutant ICAM-1 cDNA controlled by the promoter, splice signals and polyadenylation signal from the SV40 early region was constructed. The hamster DHFR gene was isolated for the plasmid pBR322DHFR (Mulligan, R. C. et al., *Proc. Natl. Acad. Sci. USA* 78:2072–2076 (1981)) by digestion with FspI and HindIII, followed by blunt-end ligation into pSV2gpt (Mitchell, P. J. et al., *Mol. Cell. Biol.* 6:425–440 (1986)) cleaved with BamHI/HindIII. The mutant sICAM-1 (soluble ICAM-1) cDNA was isolated by digestion with NotI. The ends were then filled in using Klenow, and the molecules were digested with HindIII. The molecules were then ligated into the pBR322DHFR expression vector (prepared by digestion with ApaI, ends then filled in with Klenow, and digested with HindIII to remove the ot gene). Thus, the sICAM-1 gene was physically linked to the hamster DHFR gene in an SV40-based expression vector.

The completed vector was then transfected into Chinese hamster ovary (CHO) KI DUX-B11 cells using the calcium phosphate coprecipitation method (Graham, F. L. et al., *Virology* 52:456–467 (1973)). After two days of growth in nonselective medium, the cells were passaged in selective medium containing 0.05 to 2 µM methotrexate, but lacking hypoxanthine and thymidine. Clones were then isolated, subcloned, and tested for sICAM-1 production by ELISA. Colonies secreting the greatest quantity of sICAM-1 were then subjected to two further rounds of gene amplification, and a stable cell line, designated CH0118A, was derived. This cell line, which is a preferred source of sICAM-1, secreted sICAM-1 into the culture supernate to approximately 1 µg/ml.

sICAM-1 was purified from supernates of CH0118A cells by immuno-affinity chromatography with anti-ICAM-1 monoclonal antibody R6.5. For this purpose, R6.5 was covalently coupled to CNBr-activated Sepharose 4B (Pharmacia LKB) to a final concentration of 5 mg per ml of packed resin according to the manufacturers instructions. All chromatographic steps were done at 4° C., and all buffers contained 0.2 U/ml aprotinin and 1 mM phenylmethysulfonyl fluoride. One liter of filtered supernate containing approximately 1 mg of sICAM-1 was loaded onto a 30 ml column of R6.5-Sepharose at a flow rate of 1 ml/min. The column was then washed with 200 ml of 10 mM Tris/0.15 M NaCl at a flow rate of 2.5 ml/min to remove unbound material. The bound sICAM01 was eluted with 50 mM triethylamine/0.15 M NaCl/pH 11.0 at a flow rate of 1 ml/min. Fractions were collected and immediately neutralized by the addition of 1 M Tris, pH 6.0 to a final concentration of 20 mM.

Fractions containing the eluted sICAM-1 were identified by SDS-PAGE on 10%–15% polyacrylamide gradient gels followed by silver staining. Electrophoresis and staining were done using a Pharmacia Phastgel system and silver staining kit according to the manufacturer's instructions. The fractions containing sICAM-1 were pooled and concentrated approximately 10-fold using Centricon-30 microconcentrators (Amicon, Danvers, Mass.).

The protein content of one batch of purified sICAM-1 was determined using a Bio-Rad Protein Assay according to the manufacturer's instructions (Bio-Rad Laboratories, Richmond, Calif.), and this material was frozen in aliquots for use as reference standards. Subsequently, the concentration of sICAM-1 in samples was determined in a "sandwich" type ELISA using those reference standards and two anti-ICAM-1 monoclonal antibodies, R6.5 and R6.1 (Rothlein, R. et al., *J. Immunol.* 141:1665–1669 (1988)), that bind to nonoverlapping epitopes (Marlin, unpublished data). R6.1 was bound to the plastic in 96-well plates (Nunc Immunoplate) by incubating 100 ul of a 10 ug/ml solution for 1 hour at 37° C. Each of the following steps was then done with 100 ul of reagent incubated at 37° C. for 20 min, followed by washes with phosphate buffered saline: (1) binding of serial dilutions of reference standard sICAM-1 or unknowns, (2) binding of biotinylated R6.5 (1 µg/ml), and (3) binding of horseradish peroxidase-conjugated streptavidin (Zymed Laboratories, South San Francisco, Calif.) at the manufacturer's recommended concentration. After the addition of the substrate ABTS (Zymed), and incubation for 20 min at room temperature, the absorbance was determined at 410 nm. The concentration of sICAM-1 was then determined by comparison to the reference standard curve.

The radiolabeled rhinovirus binding assay was performed using a modification of the method of Abraham and Colonno (Abraham, G. et al., *J. Virol.* 51:340–345 (1984)). Briefly, HeLa cells were infected with HRV14 for 4–6 hrs. in methionine-free RPMI 1640 supplemented with 20 m mM $MgCl_2$ and 2 mM glutamine, followed by incubation in the same medium containing 2% fetal calf serum and 100 µCi/ml [$^{35}$S]-methionine until generalized cytophatic effect was observed (usually 18 hours post-infection). After three cycles of freezing and thawing, virus in the supernate was precipitated with polyethylene glycol and recovered by centrifugation. In a modification of the published method, radio-labeled virus was then recovered by pelleting through a 30% sucrose step gradient (34,900 rpm for 2 hours in a Beckman SW41 rotor. Binding of radiolabeled virus ($1\times10^4$ cpm) to HeLa cells (confluent 24-well plates) was done as described by Abraham and Colonno (Abraham, G. et al., *J. Virol.* 51:340–345 (1984)), except that sequential washes with 1% Triton X-100 and hot 9 M urea were used to solubilize the cells and bound virus prior to scintillation counting. In typical experiments, approximately 25%–30% of input cpm bound to cells.

Using the above-described first purification procedure, milligram quantities of sICAM-1 were purified to greater than 95% purity. The purified sICAM-1 had an apparent relative molecular mass ($M_r$) of 82,000, consistent with the predicted size of a molecule containing all five extracellular Ig-like domains. The purified sICAM-1 bound to three distinct monoclonal antibodies raised against membrane-bound ICAM-1 (mICAM-1); RR1/1, R6.5, and CL203. These antibodies bind to topographically distinct sites as assessed by competitive binding assays, and their binding to sICAM-1 suggests that it maintains an overall configuration similar to native mICAM-1.

The ability of purified sICAM-1 to act as an inhibitor of rhinovirus infection was determined in quantitative in vitro virus cyto-pathic effect (CPE) assays (Staunton, D. E. et al., *Cell* 56:849–853 (1989)).

For this experiment, the major group serotype HRV54 (100 $TCID_{50}$) was plated onto HeLa cells in the presence of the indicated concentrations of sICAM-1 (or an equivalent dilution of a buffer control from the same purification run) and the cytopathic effect was determined after 4 days as previously described (Staunton, D. E. et al., *Cell* 56:849–853 (1989)).

Figure 10:
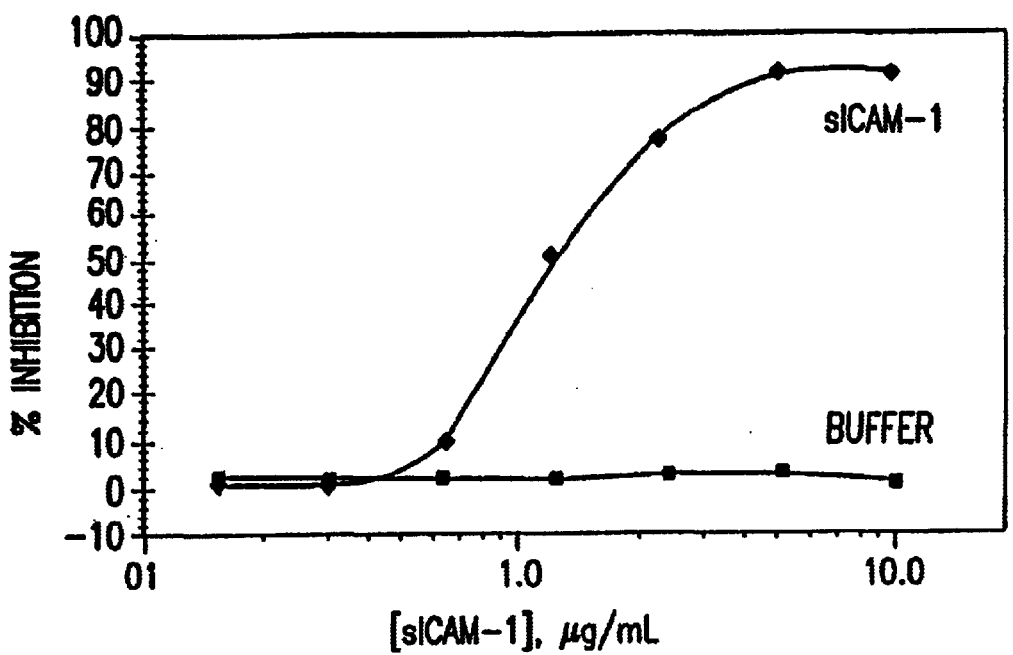
FIG. 10 shows that sICAM-1 inhibits the cytopathic effect induced by a major group Rhinovirus.

As shown in FIG. 10, sICAM-1 was a potent inhibitor of the major group human rhinovirus strain 54 (HRV54): sICAM-1 at 1 µg/ml significantly inhibited CPE (approximately 50%), and greater than 90% inhibition was achieved at 10 µg/ml. In contrast, a buffer control derived from column fractions adjoining the sICAM-1 peak had no effect.

The specificity of inhibition by sICAM-1 was tested using representatives of both the major and minor subgroups of rhinovirus, other picornaviruses, and Herpes Simplex Virus type-1 (HSV-1), an unrelated enveloped DNA virus.

For this experiment, purified sICAM-1 (5 µg/ml) was plated on HeLa cells wit the indicated viruses (100 $TCID_{50}$), and cytopathic effect determined after 4 days: HRV54 (major group rhinovirus), HRV2 (minor group rhinovirus), Cox. A13 (Coxsackie A13, picornavirus using major group receptor), Cox. B1 (Coxsackie B1, does not use major group receptor), Polio (Poliovirus I), HSV-1 (Herpes Simplex Virus, type-1).

Figure 11:
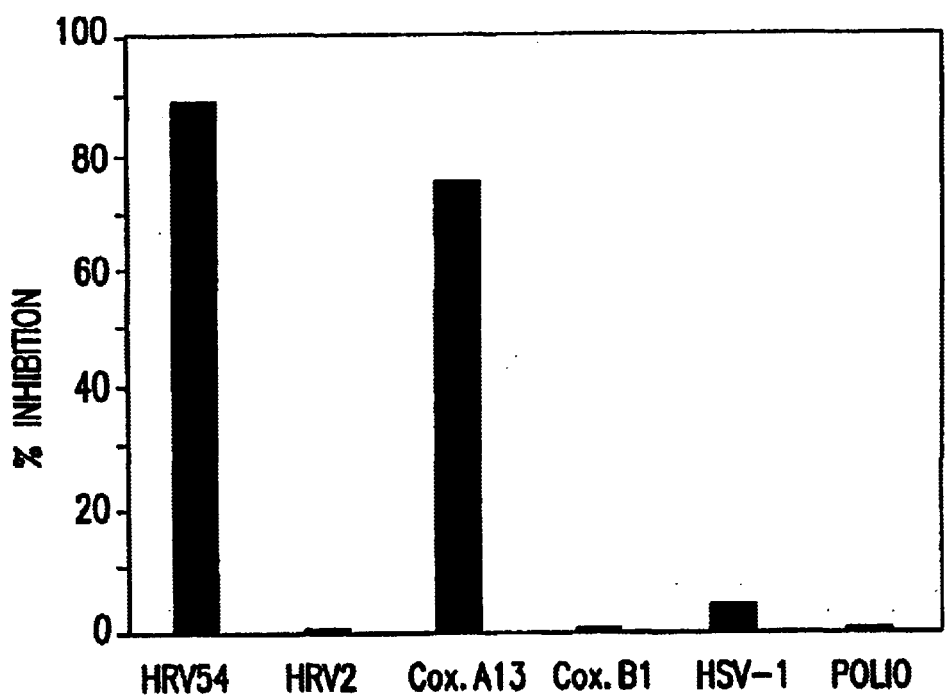
FIG. 11 shows that purified sICAM-1 specifically inhibits CPE induced by picornaviruses which utilize the rhinovirus major group receptor.

As shown in FIG. 11, sICAM-1 inhibited HRV54, but had no significant effect on HRV2, a minor group strain that does not utilize ICAM-1 as a cellular receptor. In addition, sICAM-1 inhibited infection by Coxsackie A13, another picornavirus known to use ICAM-1 as a receptor (Colonno, R. J. et al., p. 93–102, *Positive Strand RNA Viruses*, (Alan R. Lis, Inc.)). In contrast, sICAM-1 did not inhibit Poliovirus, Coxsackie B1 (picornaviruses that do not bind via ICAM-1), or HSV-1.

The specificity of virus inhibition indicated that sICAM-1 did not prevent infection via generalized effects on the cell's ability to support viral replication, but rather through inhibition or virion binding. This was determined by measuring the effect of sICAM-1 on virus binding using a $^{35}$S-methionine-labeled virus binding assay.

For this experiment, [$^{35}$S]-methionine labeled HRV14 was mixed with the indicated concentrations of sICAM-1, a chromatography buffer control, or the anti-ICAM-1 monoclonal antibodies CL203 or R6.5 at 200 µg/ml. As previously shown, antibody R6.5 inhibits the interaction of ICAM-1 with either LFA-1 or HRV54, while antibody -CL203 does not (Staunton, D. E. et al., *Cell* 56:849–853 (1989)). After preincubation for 30 min at 4° C., the mixture was plated on HeLa cells and the bound cpm determined after washing.

Figure 12:
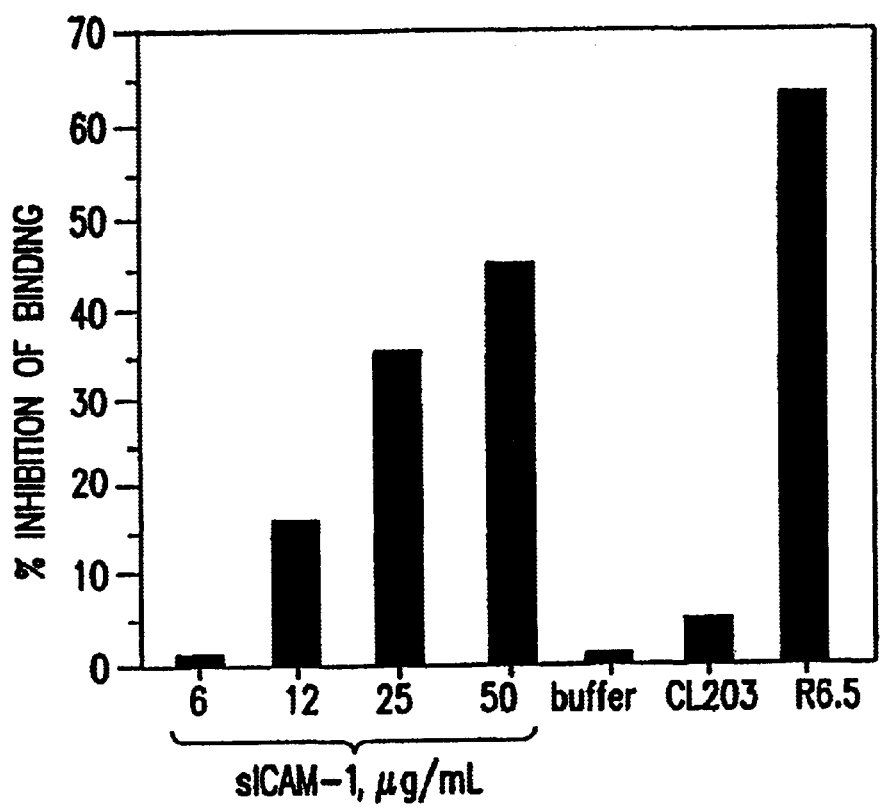
FIG. 12 shows that purified sICAM-1 inhibits the binding of rhinovirus virions to cells.

As shown in FIG. 12, sICAM-1 inhibited the binding of HRV14 (major rhinovirus subgroup) in a dose-dependent manner, while the buffer control had no effect. The positive control anti-ICAM-1 Mab R6.5 was also effective, while the negative control Mab CL203 (which binds to ICAM-1 but does not inhibit functions) had no significant effect (see also, Staunton, D. E. et al., *Cell* 56:849–853 (1989)). It should be noted that the virus binding assay uses a substantially higher concentration of virus particles than the CPE assay, which might account for the lower degree of inhibition of binding compared to CPE.

The ability to produce large amounts of purified sICAM-1 permits X-ray crystallographic studies, and resolution of the 3-dimensional structure of the molecule. The use of purified sICAM-1 enables the development of assays to facilitate the design or detection of anti-rhinoviral agents.

These experiments show that sICAM-1 is a potent and specific inhibitor of major group rhinovirus infection. sICAM-1 was found to be able to inhibit HRV54, a major group virus, but did not inhibit HRV2, a member of the minor group of rhinoviruses which do not utilize ICAM-1 as a receptor. The anti-viral activity of sICAM-1 indicates that sICAM-1, or one of its functional derivatives could be employed in anti-viral therapy. The ICAM-1 binding site on the virus is highly conserved (Rossman, M. G., *J. Biol. Chem.* 264:14587–14590 (1989)) and likely to be functionally constrained in its ability to mutate. Thus, a drug directed at the site of ICAM-1-virus interaction would have the dual advantages of intervening at the sensitive first stage of virus infection, combine with a limited ability of the virus to escape neutralization through the generation of drug-resistant variants.

The data demonstrates that sICAM-1 can block the infectivity of the major group of rhinovirus in vitro, and indicate that sICAM-1 may have therapeutic effects in attenuating or preventing consequences of rhinovirus infection.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of diagnosing the presence of viral infection, comprising:
   (a) contacting a biological sample suspected of containing a virus with a detectably labeled and soluble ICAM-1 functional derivative for a time and under conditions sufficient for the formation of detectable complexes of said ICAM-1 functional derivative and said virus; and
   (b) determining the presence of said complexes in said sample, wherein
      (i) said virus is a major serotype rhinovirus;
      (ii) said soluble functional derivative of ICAM-1 lacks a transmembrane domain and comprises (1) domains 1–2 of ICAM-1 or (2) a variant of domains 1–2 of ICAM-1; and
      (iii) said soluble functional derivative of ICAM-1 is capable of binding major serotype human rhinovirus; wherein said soluble functional derivative of ICAM-1 contains the following amino acids at the indicated position: Q1T, V4, R13, D26QPK, K39KE, G46NN, R49KV, Q58EDS, D60, D71GQS, K77T, E87, N103, A155N, R166PQ, N175TSA and S177; wherein said amino acids are defined in terms of native ICAM-1 consisting of the amino acid sequence of FIG. 1.

2. A method of diagnosing the presence of viral infection, comprising:
   (a) contacting a biological sample suspected of containing a virus with a detectably labeled and soluble ICAM-1 functional derivative for a time and under conditions sufficient for the formation of detectable complexes of said ICAM-1 functional derivative and said virus; and
   (b) determining the presence of said complexes in said sample, wherein
      (i) said virus is a major serotype rhinovirus;
      (ii) said soluble functional derivative of ICAM-1 lacks a transmembrane domain and comprises domains 1–2 of ICAM-1; and
      (iii) said soluble functional derivative of ICAM-1 is capable of binding major serotype human rhinovirus; wherein the amino acid sequence of said soluble fragment is amino acids 1 to 451 of FIG. 1, followed by a phenylalanine (F).

3. A method of diagnosing the presence of viral infection, comprising:
   (a) contacting a biological sample suspected of containing a virus with a detectably labeled and soluble ICAM-1 functional derivative for a time and under conditions sufficient for the formation of detectable complexes of said ICAM-1 functional derivative and said virus; and
   (b) determining the presence of said complexes in said sample, wherein
      (i) said virus is a major serotype rhinovirus;
      (ii) said soluble functional derivative of ICAM-1 lacks a transmembrane domain and comprises (1) domains 1–2 of ICAM-1 or (2) a variant of domains 1–2 of ICAM-1; and
      (iii) said soluble functional derivative of ICAM-1 is capable of binding major serotype human rhinovirus; wherein said soluble functional derivative of ICAM-1 contains at least one of the following amino acid substitutions at the indicated position: S3/T; K8/E; R13/K; G15/SA; Y52/F; S61/I; Q62PM/API; M64/I; Y66/T; N68/K; D71/E; S74/A; T75/A; R88V/EA; E90/Q; L91/A; N118/Q; R125/E; E127/R; K128/R; V136GE/GVK; N156/E; A178/G; A189T/SI; and D203TQ/TAD, wherein said amino acid substitution is defined in terms of native ICAM-1 consisting of the amino acid sequence of FIG. 1.

* * * * *

UNITED STATES PATENT AND TRADEMARK OFFICE
CERTIFICATE OF CORRECTION

PATENT NO. : 6,777,191 B1
DATED : August 17, 2004
INVENTOR(S) : Springer et al.

It is certified that error appears in the above-identified patent and that said Letters Patent is hereby corrected as shown below:

Title page,
Item [56], References Cited, FOREIGN PATENT DOCUMENTS, please add:
-- EP 0289949  11-09-1988  Europe --
OTHER PUBLICATIONS, please add:
-- Tomassini, J., "Isolation, characterization, and cloning of the cellular receptor for the major group of human rhinoviruses,
Dissertation Abstracts International, B. 47:2774-B (1987)
White, J.M. & Littman, D.R., "Viral Receptors of the Immunglobulin superfamily," Cell 56:839-847 (1989) --

Signed and Sealed this

Seventh Day of June, 2005

JON W. DUDAS
*Director of the United States Patent and Trademark Office*